United States Patent [19]
Cheung et al.

[11] Patent Number: 5,976,792
[45] Date of Patent: *Nov. 2, 1999

[54] **REGULATION OF EXOPROTEIN IN *STAPHYLOCOCCUS AUREUS***

[75] Inventors: Ambrose Cheung, New York; Vincent A. Fischetti, West Hempstead, both of N.Y.

[73] Assignee: Siga Pharmaceuticals, Inc., New York, N.Y.

[*] Notice: This patent is subject to a terminal disclaimer.

[21] Appl. No.: 08/676,782

[22] Filed: Jul. 8, 1996

Related U.S. Application Data

[63] Continuation-in-part of application No. 08/248,505, May 24, 1994, Pat. No. 5,587,288.
[51] Int. Cl.$^6$ ............... C12Q 1/68; C07H 21/04; C12N 15/74; C07K 14/31; C07K 16/12
[52] U.S. Cl. ............... 435/6; 435/320.1; 530/350; 530/387.1; 530/388.1; 530/388.4; 530/825; 536/237; 536/24.32; 935/6; 935/77; 935/78
[58] Field of Search ............... 435/6, 320.1; 536/23.7, 536/24.32; 935/6, 77, 78; 530/350, 387.1, 388.1, 388.4, 825

[56] References Cited

U.S. PATENT DOCUMENTS 5,587,288  12/1996  Cheung et al. ............... 435/6

OTHER PUBLICATIONS

J. Sambrook et al. "Molecular Cloning, a Laboratory Manual" Cold Spring Harbor Laboratory Press, Cold Spring Harbor, New York 1989 pp. 17.2–17.44.

S. Wnendt et al., "Characterization of the gene encoding α–sarcin, a ribosome–inactivating protein secreted by *Aspergillus giganteus*," Gene (1993) 124:239–244.

L. Sarada Nandivada et al. "SAR–2: Identification of a novel plasmid–encoded β–lactamase from India" *FEMS Microbiology Letters* (1989) 57:219–222.

K. Lawton et al., "Acquired Resistance Signal Transduction in Arabidopsis is Ethylene Independent" *The Plant Cell* (1994) 6:581–588.

A. Cheung et al., "Regulation of exoprotein expression in *Staphylococcus aureus* by a locus (sar) distinct from agr" *Proc. Natl. Acad. Sci. USA* (1992) 89:6462–6466.

A. Camilli et al., "Insertional Mutagenesis of *Listeria monocytogenes* with a Novel Tn917 Derivative That Allows Direct Cloning of DNA Flanking Transposon Insertions", *Journal of Bacteriology*, (1990) 172:3738–3744, No. 7.

A. Cheung et al., "Cloning and Sequence of sarA of *Staphylococcus aureus*, a Gene Required for the Expression of agr" *Journal of Bacteriology* (1994) 176:4168–4172, No. 13.

E. McConkey, "Human Genetics, The Molecular Revolution" Jones and Barlett Publications, Boston (1993) p. 33.

A. Cheung, "Diminished Virulence of a sar$^-$lagr$^-$ Mutant of *Staphylococcus aureus* in the Rabbit Model of Endocarditis", *The Journal of Clinical Investigation, Inc.* (1994) 94:1815–1822.

Archer et al. Antimicrobial Agents and Chemotherapy 38(3):447–454, Mar. 1994.

*Primary Examiner*—Stephanie Zitomer
*Attorney, Agent, or Firm*—Burns, Doane, Swecker & Mathis, L.L.P.

[57] ABSTRACT

The present invention provides a staphylococcal accessory regulatory protein sar, and the gene encoding that protein (sar). This protein relates to the recognition and control of bacterial infections, particularly infections caused by *Staphylococcus aureus* (*S. aureus*). The sar protein and gene are thus useful in preventing or treating staph infections, and in diagnostic kits and assays for detecting the presence of the sar protein and sar gene.

30 Claims, 10 Drawing Sheets

Fig. 2

```
  1  AATAGGGAGGTTTTAAACATGGCAATTACAAAAATCAATGATTGCTTTGAGTTGTTATCA    60
                       METAlaIleThrLysIleAsnAspCysPheGluLeuLeuSer

ATGGTCACTTATGCTGACAAATTAAAAAGTTTAATTAAAAAGGAATTTTCAATTAGCTTT   120
 15  METValThrTyrAlaAspLysLeuLysSerLeuIleLysLysGluPheSerIleSerPhe

GAAGAATTCGCTGTATTGACATACATCAGCGAAAACAAAGAGAAAGAATACTATCTTAAA   180
 35  GluGluPheAlaValLeuThrTyrIleSerGluAsnLysGluLysGluTyrTyrLeuLys

GATATTATTAATCATTTAAACTACAAACAACCACAAGTTGTTAAAGCAGTTAAAATTTTA   240
 55  AspIleIleAsnHisLeuAsnTyrLysGlnProGlnValValLysAlaValLysIleLeu

TCTCAAGAAGATTACTTCGATAAAAAACGTAATGAGCATGATGAAAGAACTGTATTAATT   300
 75  SerGlnGluAspTyrPheAspLysLysArgAsnGluHisAspGluArgThrValLeuIle

CTTGTTAATGCACAACAACGTAAAAAAATCGAATCATTATTGAGTCGAGTAAATAAACGA   360
 95  LeuValAsnAlaGlnGlnArgLysLysIleGluSerLeuLeuSerArgValAsnLysArg

ATCACTGAAGCAAACAACGAAATTGAACTATAA
115  IleThrGluAlaAsnAsnGluIleGluLeu---
```

| | | | | |
|---|---|---|---|---|
| SarA | 17 | TYADKLKSLIKKEFSISFEEFAV | 39 | |
| | | +Y+++ + L KK F +S EE ++ | | |
| VirF | 93 | SYSEEKRGLNKKIFLLSEEEVSI | 115 | |
| SarA | 43 | ISENKEKEYYLKDIINHLNYKQPQVVKAVK | 72 | |
| | | + +N EK + L DI N+LN + V K ++ | | |
| VirF | 167 | VEKNIEKRWRLSDISNNLNLSEIAVRKRLE | 19 | |

FIG. 3

```
   1  AAAGCGTTGATTTGGGTAGTATGCTTTGACACAACAAATTTTAATTTAGC

51  AAATTCGATAGTCAACTCATTCTTAAGACC TAAATTAATGTTATTTTTA
          UP                -35                        -10
 101  ATAATTTA CACCAAATTAAT AGCAAA AATTATGTTATTCGTGC TAATAT T
         ▼+1                         P2
 151  TCATAGTTGGTTATTCAATTAATTAAAAATAAGTCAAATGCACAACTTT
                                                ORF4 >
 201  TTATAATTCATTGAGTCGAGTTTGAAAAATAAAAGTGCTTTAATGCATGA
 251  TCAATTATCGTACTTCTATTATTTGTTACCCGTTATCAATCGGAATAAC
            IR6                 IR5                  IR6
 301  GTATAGACACTTTAACGTGCTATAGATTGGTTTTAATCACTAAATTAATG
                       IR5                   --------->
 351  TGTTTTTCTTATCATTAAAACTGCACTGAGAATTAC TAAATTAAAAAAAT
                                             --------->
         UP        IR4            -35           IR4    -10
 401  TATAAAAATTTTT CATTTTT AGTGATA AAATTCTGAAAAAT GGGTAT AAA
                ▼+1                          P3
 451  TAGTAGAAGAAGTTAACTTGGAAGAGTTAAGCTATAACAAAGAATCTCTT
 501  TAGACACACATTGAATATCGAAACATTTAATTGCGCTAAATCGTTTCATT
            IR3                         SD    IR3     ORF3 >
 551  AAATAAATTACCTTGTATTGTCGATTAAATT AAGG TAAATTATAAAAAAT

601  GCTGATATTTTGACTAAACCAAATGCTAACCCAGAAATACAATCACTGT
                              IR2      IR2            -35
 651  GTCTAATGAATAATTTGTTTTATAAACACTTTTTTG TTTACT TCTCATTT
                                                       P1
          < ORF3
              -10      ▼+1              IR1
 701  TTAATTAGT TATAAT TAACTAAATAATAGAGCATTAAATATATTTAATAA
                  IR1
 751  AACTTATTTAATGCAAAATTATGACTAACATATCTATAATAAATAAAGAT
 801  TAGATATCAATATATTATCGGGCAAATGTATCGAGCAAGATGCATCAAAT
             SD           sarA >
 851  AGG GAGG TTTTAAACATGATGGCAATTACAAAAATCAATGATTGCTTTGA
 901  GTTGTTATCAATGGTCACTTATGCTGACAAATTAAAAAGTTTAATTAAAA
 951  AGGAATTTTCAATTAGCTTTGAAGAATTCGCTGTATTGACATACATCAGC
1001  GAAAACAAAGAGAAAGAATACTATTTTAAGATATTATTAATCATTTAAA
1051  CTACAAACAACCACAAGTTGTTAAAGCAGTTAAAATTTTATCTCAAGAAG
1101  ATTACTTCGATAAAAACGTAATGAGCATGATGAAGAACTGTATTAATT
1151  CTTGTTAATGCACAACAACGTAAAAAAATCGAATCATTATTGAGTCGAGT
1201  AAATAAATGAACTGAAGCAAACAACGAAATTGAACTATAATTTTGTTTAG
                               sart
1251  CGCAATTTGGTGAAGTTTGATAGATGATACATTCTATTAAACTTCCTTTT
           *
1301  TTTATGCTCTTTTTACCTAATTGTTAAGAGGTTTTGCACTAATGGCACT
```

A

```
 866    ATGGCAATTACAAAAATCAATGATTGCTTTGAGTTGTTATCAATGGTCAC
               ──────────────▶──────────────▶
 916    TTATGCTGACAAATTAAAAAGTTTAATTAAAAAGGAATTTTCAATTAGCT

966    TTGAAGAATTCGCTGTATTGACATACATCAGCGAAAACAAAGAGAAAGAA
                         C
1016    TACTATTTTAAAGATATTATTAATCATTTAAACTACAAACAACCACAAGT

1066    TGTTAAAGCAGTTAAAATTTTATCTCAAGAAGATTACTTCGATAAAAAAC

1116    GTAATGAGCATGATGAAAGAACTGTATTAATTCTTGTTAATGCACAACAA
                                                    C
1166    CGTAAAAAAATCGAATCATTATTGAGTCGAGTAAATAAATGA
```

B

```
  1    MAITKINDCFELLSMVTYADKLKSLIKKEFSISFEEFAVLTYISENKEKE
       ::::::::::::::::::::::::::::::::::::::::::::::::::
  1    MAITKINDCFELLSMVTYADKLKSLIKKEFSISFEEFAVLTYISENKEKE

51    YYLKDIINHLNYKQPQVVKAVKILSQEDYFDKKRNEHDERTVLILVNAQQ
       :: :::::::::::::::::::::::::::::::::::::::::::::::
 51    YYFKDIINHLNYKQPQVVKAVKILSQEDYFDKKRNEHDERTVLILVNAQQ

101    RKKIESLLSRVNKRITEANNEIEL         RN450, DB
       ::::::::::::
101    RKKIESLLSRVNK                    RN6390
```

Fig. 4

A
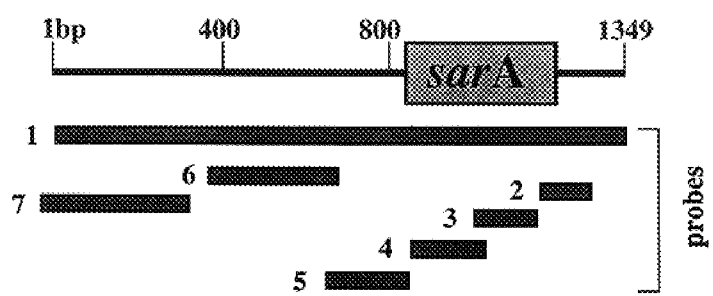
B
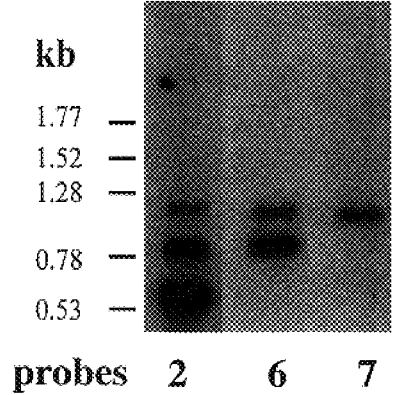
Fig. 5

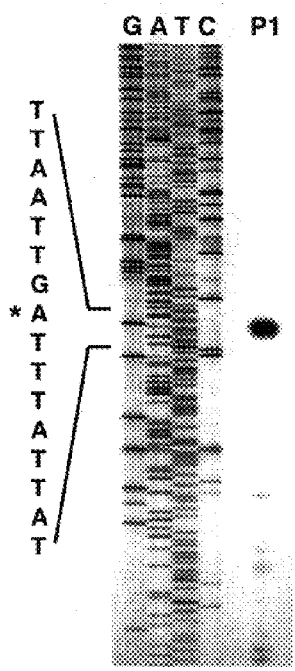
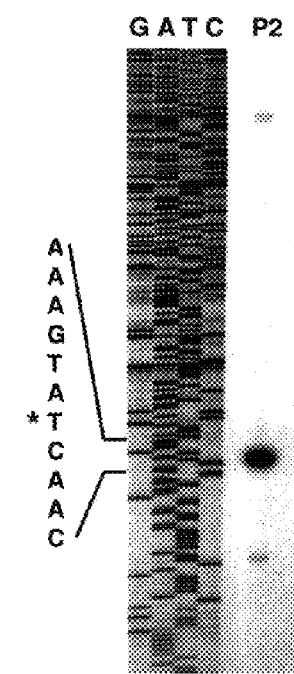
Fig. 6

Fig. 9

DNA and Amino Acid Sequence of SAR 6390S

```
     950        960        970        980        990       1000
      |----------|----------|----------|----------|----------|
     ATGCTGATATTTTTGACTAAACCAAATGCTAACCCAGAAATACAATCACTGTCTAATG
      M  L  F  L  T  K  P  N  A  N  P  E  I  Q  S  L  C  L  M 1010       1020       1030       1040       1050       1060
      |----------|----------|----------|----------|----------|
     AATAATTTGTTTTATAAACACTTTTTTGTTTACTTCTCATTTTAATTAGTTATAATTAA
      N  N  L  F  Y  K  H  F  F  V  Y  F  S  F  L  I  S  Y  N
```

Alignment of the sarA proteins of S. aureus and S. epidermidis

```
S. aureus     MAITKINDCFELLSMVTYADKLKSLIKKEFSISFEEFAVLTYISENKEKE           - 50
              :: :::::::::::::::: :: ::::::::::::: ::::::::::
S. epidermidis MAISKINDCFELLAMVTYADRLKGIIKKEFSISFEEFRVLTYISENKEEE S. aureus     YYLKDIINHLNYKQPQVVKAVKIL SQEDYFDKKRNEHDERTVLILVNAQQ          - 100
              ::::::::::::::::::::::::: :: :: ::::::::::::: :: :
S. epidermidis YYLKDIINHLNYKQPQVVKAVKNLSQENYFNKKRNEHDERTVL ILVDSKQ S. aureus     RKKIESLLSRVNK RITEANNE IEL              - 124
              :::: :: :: :::::::: :: :
S. epidermidis RKKIDDLLKRVNNRITEANNENEV
```

S. aureus     pI = 8.52   M.W. = 14.7 kDa
S. epidermidis pI = 8.53   M.W. = 14.8 kDa

Fig. 10 ion Ser. No. 08/248,505, filed May 24, 1994 now U.S.

REGULATION OF EXOPROTEIN IN STAPHYLOCOCCUS AUREUS

RELATED APPLICATIONS

This application is a continuation-in-part of U.S. application Ser. No. 08/248,505, filed May 24, 1994 now U.S. Pat. No. 5,587,288.

BACKGROUND OF THE INVENTION

1. Field of the Invention

This invention relates to the recognition and control of bacterial infections, particularly infections caused by *Staphylococcus aureus* (*S. aureus*). More particularly, the present invention provides a staphylococcal accessory regulatory protein sarA, and the gene encoding that protein (sar).

2. Description of the Related Art

Septicemia due to *Staphylococcus aureus* is often the consequence of a local infection that has gained access to the bloodstream. Once the bacteria enter the bloodstream, patients are at a risk of developing a range of infections from endocarditis, pneumonia, meningitis, and sepsis to severe toxemia (including toxic shock syndrome) and other life-threatening metastatic complications. Although the use of newer antimicrobial agents has initially controlled some of these infections, the recent emergence of multiple-drug resistance in *S. aureus* has made many currently available antimicrobial agents (including fluoroquinones) ineffective, thereby posing an important public health problem. Thus, there is an urgent need for alternative approaches in the treatment of *S. aureus* infections.

Infections caused by *S. aureus* are probably related to the organism's striking capability to react to changing environments during the infection process. In any stage of surface colonization, entry, and invasion, this highly coordinated response seems to be modulated by the expression of appropriate genes via signal transduction pathways.

One potentially effective mechanism for dealing with the emergence of antibiotic resistance among *S. aureus* strains is the development of safe and effective vaccines. However, experimental data justifying a direct vaccine strategy are presently lacking. An alternative approach is to consider targeting regulatory loci that are involved in the control and expression of potential virulence determinants (e.g., hemolysins and fibrinogen and fibronectin binding proteins).

Postexponential phase expression in bacteria is generally governed by global regulatory systems in which a common regulator controls the activities of several unlinked genes. Many exoproteins normally synthesized and secreted during the postexponential phase in *S. aureus* are virulence factors. In contrast, synthesis of a number of surface proteins (e.g., protein A, coagulase, and fibronectin binding proteins) that clearly play a role in staphylococcal infections is repressed postexponentially. The regulation of virulence determinants and other exoprotein genes in *S. aureus* involves at least three global regulatory systems, including agr, xpr, and sar.

The agr locus controls production of extracellular and cell wall proteins that appear to play a role in virulence (e.g., hemolysins, coagulase, and protein A). Most of the exoprotein regulated by agr are either not synthesized or synthesized at a reduced rate in agr mutants while the synthesis of surface proteins is upregulated (11). The agr locus has been cloned (id.) and consists of at least five genes, agrA, agrB, agrC, agrD and the hld (β-hemolysin) gene. Sequence analysis indicated that it has features suggestive of a two component regulatory system as described in other procaryotes (11). In particular, the agrB is the signaling component while agrA corresponds to the transcription activation element (11, 14). The agr locus is composed of two divergent transcription units designated RNAII (agr A,B,C and D genes) and RNAIII (hld gene). Mutations in either agrA or agrB has led to decreased transcription of RNAIII (11, 16), which also encodes the 26 residue hemolysin polypeptide, is essential for the transcriptional control of exoprotein synthesis (e.g. α-hemolysin) (11).

The xpr locus, like that of agr, also positively regulates exoprotein synthesis. Smeltzer et al. reported that two sets of agr and xpr mutants with different genetic backgrounds were less lethal and their corresponding parents in a mouse peritonitis model (Smeltzer et al. 1993. *Infect. Immun.* 61:919–925); however, a very high challenging inoculum ($10^9$-$10^{10}$ CFU) was required for lethality in this study. Furthermore, both xpr and agr mutants produced greatly reduced amount of hemolysin. This finding together with the observation that the RNAIII level is decreased in a xpr mutant suggest that the xpr and agr loci may behave as interactive regulatory genes (9,20).

An additional locus in *S. aureus*, designated sar, that is involved in the regulation of exoproteins has been reported (3). Inactivation of this locus by Tn917LTV1 insertion has resulted in decreased expression of several extracellular (e.g. β-hemolysin) and cell wall proteins (3). Phenotypic, Southern blot and genetic mapping analyses indicated that this locus is distinct from agr and xpr (3,4). Using the DNA sequence flanking the Tn917LTV1 insertion as a probe, the sar gene that is involved in the regulation of exoprotein synthesis has been cloned and sequenced. Additional transcriptional and phenotypic studies revealed that this sar gene is necessary for the optimal expression of agr.

Inactivation of the sar locus has resulted in alterations of expression of exoproteins in three different *S. aureus* isolates (strains DB, RN6390 and RN450) (3,4). Using both α and β hemolysin genes as probes, transcriptional studies of strains with well-defined genetic backgrounds (i.e. RN6390 and RN450) revealed that the sar locus probably regulates exoprotein genes positively at the MRNA level (4). The regulation of exoprotein genes (e.g.α and β-hemolysins) by the sar locus in vitro was found to begin at midlog phase and continued onto the postexponential phase (4). This mode of regulation is similar to that of agr on target exoprotein gene transcription.

To elucidate the interaction between the sar and agr loci, the level of the RNAIII transcript in sar mutants as well as mutants complemented was assayed with an intact sarA gene. The data suggested that the levels of RNAIII were related to a functional sarA gene (FIG. 2). It was also found possible to overcome the deficiency in β and α hemolysin expression in a sar mutant by introducing a plasmid carrying RNAIII under the control of a promoter uninfluenced by sar. To rule out the possibility of some concerted interaction, Northern blot analysis was employed to determine that the level of sar mRNA did not appear to be altered appreciably in an agr background (RN6911) (11) as compared to the wild type parent RN6390. Taken together, these data suggest that the agr locus is under the control of sar.

Analysis of the sarA gene sequence leads to several interesting observations. First, there is no helix-turn-helix motif identifiable in a protein sequence that has a predicted cL helical conformation. Secondly, glycine residues which are frequently found in helix-turn-helix motif (1) as well as in two component signal transduction systems (14) are noticeably absent. Third, a small molecular size together with a high percentage of charged residues (33%) and a basic charge are molecular properties that are consistent with those found in other DNA binding proteins (21). Fourth, in contrast to the agr locus, direct sequence comparison of the sarA gene with prototypic sensor and activator genes in E. coli, S. typhimurium and B. subtilis did not reveal any significant similarity to two component regulatory systems (14). Finally, sequence similarity with virF, which is a positive regulator of invasive genes in a regulon carried on a large plasmid in Shigella flexneri (8,18), is of comparative interest. Like that of virF which regulates target genes via the control of another positive regulatory gene virB, the sarA gene may govern the expression of exoprotein genes (e.g. α and β hemolysins) by positively controlling the level of RNAIII. However, the exact mechanism by which the sarA gene product interacts with the agr locus is not apparent from the sequence analysis.

The postexponential regulation of exoprotein genes in S. aureus involves at least three global regulatory systems (sar, agr and xpr). Although the evidence suggests that the sarA gene may control exoprotein synthesis via the control of agr, the relationship between sarA and xpr is not clear. Nevertheless, the observation that both agr and xpr mutants produce greatly reduced amounts of RNAIII transcript has led to the idea that agr and xpr loci may behave as interactive regulatory genes. It is therefore, conceivable that the sarA may interact with the xpr locus as well.

It should be noted, however, that the restoration of RNAIII transcript (FIG. 8) upon the introduction of the sarA gene into a sar mutant was never complete. This finding raised the possibility that additional signals may be required for a normal pattern of RNAIII transcription, thereby leading to optimal expression of exoproteins at postexponential phase. Based on the pattern of transcription of an exoprotein gene such as hemolysin in an agr+ parent, Vandenesch et al suggested that a separate postexponential signal independent of agr may be needed for augmented α-hemolysin transcription during the postexponential phase (22).

SUMMARY OF THE INVENTION

In general, this invention relates to the staphylococcal accessory regulatory protein sarA, and its use in regulation of virulence determinants and other exoprotein genes. Accordingly, a major object of the present invention is to provide a nucleic acid sequence of the sar gene, and the amino acid sequence of the sarA protein.

With the foregoing and other objects, advantages, and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 2 [SEQ ID NOS.: 6–9] Nucleotide sequence of the sarA gene. The ribosomal binding site is underlined. The arrow marks the site of transposon insertion. The protein sequence similarity between sarA and virF is also shown.

FIG. 3 [SEQ ID NO.: 10] The nucleotide sequence of the sar regulatory region. Shown are 890 bp upstream of the translation start codon of sarA and 200 bp downstream of the sarA stop codon. Only the start and stop codon of sarA is included. The complete sequence of sarA of strain RN6390 is given in FIG. 2. Putative ribosome-binding sites are emphasized with a double line and tagged with SD. Start and stop codons of sarA, ORF3, and ORF4 are in bold letters. The mapped 5'-ends of the mRNAs identified by primer extension and S1 nuclease protection are indicated by solid arrowheads and labeled P1, P3, or P2. The mapped 3'-end is marked by an open arrowhead. The termination site predicted by a computer program is identified by a star. The termination signal (designated sart) forming a stemloop is labeled by a broken line. Putative promoter regions are highlighted by boxed sequences and labeled −10 and −35 (core promoter) and UP (extended promoter). Broken arrows below the sequence indicate direct repeats, solid arrows above the sequence mark a structure of dyad symmetry and are numerically designated with the prefix IR (inverted repeat). The potential core target site known for DNA-binding proteins is underlined.

FIG. 4 (A) [SEQ ID NO.: 11] The nucleotide sequence of sarA of S. aureus strain RN6390. Also given is the deduced amino acid sequence of strain RN6390 aligned with that of strains RN450 and DB. (B) [SEQ ID NOS.: 12 & 13] Differences in composition are indicated by bold letters. Arrows above the sequence identify a direct repeat.

FIG. 5. Transcriptional analysis of sar. (A) Graphic representation of the location of the probes within the sequences given in FIG. 3 and 4. (B) A Northern blot of sar transcripts by probe-walking along the sar locus with PCR-generated DNA-fragments. The transcriptional pattern obtained with probe 2 is identical to that from probes 1, 3, 4 and 5.

FIG. 6. Mapping of the 5' ends of three sar transcripts by primer extension analysis. Total RNA was hybridized respectively with several oligonucleotides complementary to the mRNA in different parts of the sar locus and extended by reverse transcriptase. The precise base-mapping was done by comparing the migration of the extended product with a parallel sequencing reaction primed by an identical oligonucleotide. The sequence encompassing the initiation start (marked by stars) is enlarged on the left side. The transcription start sites of the 0.58 kb sarA (A) [SEQ ID NO.: 14], the 0.8 kb sarc (B) [SEQ ID NO.: 15], and the 1.2 kb sarB (C) [SEQ ID NO.: 16] mRNAs are labeled P1, P3, and P2, respectively.

FIG. 9 [SEQ ID NO.: 18]. DNA and amino acid sequence of SAR6390S

FIG. 10 [SEQ ID NO.: 12 & 13]. Sequence comparison of sarA proteins of *Staphylococcus aureus* and *Staphylococcus epidermidis*.

DETAILED DESCRIPTION OF THE PREFERRED EMBODIMENTS OF THE INVENTION

Figure 1A:
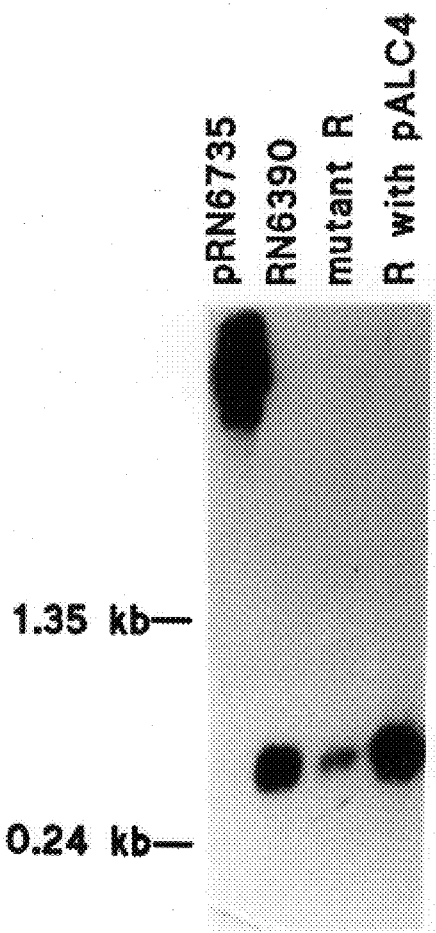
FIG. 1 Northern blots of RNAIII transcript in two sets of S. aureus strains. The first set (A) includes RN6390, mutant R and R complemented with plasmid pALC4 (carrying an intact sarA gene). The second set (B) comprises of RN450, mutant A and A complemented with pALC4. The plasmid pRN6735 is a positive control and comprises of RNAIII cloned into pRN6725 (22).

A product of this invention is a regulatory protein of *S. aureus* which controls the expression of potential virulence factors such as bacterial endotoxins. It has been designated sar for staphylococcal accessory regulator. It is useful for designing analogs which interfere with the expression of these toxins thereby, functioning as an antimicrobial agent to render the microorganism avirulent.

Through the use of the gene which expresses this protein or a fragment of said gene, a method is provided for the diagnostic identification of pathogenic staphylococci which express the protein and the resulting virulence factor. In this method, DNA is extracted from the microbial isolated suspected to be pathogenic and examined for complementary nucleotide sequences by hybridization to the molecular probe which may be labeled gene or a labeled segment thereof.

More specifically, the suspected staphylococcal isolate may be incubated with lysostaphin to digest the cell and release its DNA which is purified by any of the procedures known to the skilled artisan. The DNA is then contacted with the selected probe. Hybridization, detected by the selected label is a positive indication of the presence of the sar gene and that therefore, the strain of *S. aureus* isolated is capable of releasing toxic products.

A further aspect of the present invention provides the nucleic acids encoding the subject genes in replicable expression vectors and transformed hosts containing these vectors. The replicable expression vectors may also be used to obtain the polypeptides of the present invention by well known methods in recombinant DNA technology.

The instant replicable expression vectors comprise a nucleic acid encoding the subject gene, i.e., the coding sequence is operably linked in proper reading frame to a nucleotide sequence element which directs expression of the sar gene. In particular, the nucleotide sequence elements may include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated. The replicable expression vectors of this invention can express the sar protein at high levels. Many of these vectors are based on pBR322, M13 and lambda and are well known in the art and employ such promoters as trp, lac, $P_L$, T7 polymerase and the like. Hence, one skilled in the art has available many choices of replicable expression vectors, compatible hosts, and well-known methods for making and using the vectors.

Moreover, peptides and fragments as well as chemically modified derivatives of the sar protein are also contemplated by the present invention. Briefly, any peptide fragment, derivative or analog which retains substantially the same biological activity of the sarA protein is contemplated. An analog may be defined herein as a peptide or fragment which exhibits sar activity, but has an amino acid substitution, insertion or deletion in comparison to the wild-type sar protein. Such an analog can be prepared by the "conservative" substitution of an amino acid having similar chemical properties.

Thus, it should also be appreciated that also within the scope of the present invention are DNA sequences encoding a sar protein having the same amino acid sequence as the wild-type protein, but also those DNA sequences which are degenerate to the wild-type sequence. By "degenerate to" is meant that a different three-letter codon is used to specify a particular amino acid. It is well known in the art that the following codons can be used interchangeably to code for each specific amino acid:

| Amino Acid | Corresponding Codons |
| --- | --- |
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC or GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Termination codon | UAA (ochre) or UAG (amber) or UGA (opal) |

It should be understood that the codons specified above are for RNA sequences. The corresponding codons for DNA have T substituted for U.

Mutations can be made in the wild-type sequence such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein.

The following is one example of various groupings of amino acids:

| Amino acids with nonpolar R groups | Amino acids with uncharged polar R groups |
|---|---|
| Alanine | Glycine |
| Valine | Serine |
| Leucine | Threonine |
| Isoleucine | Cysteine |
| Proline | Tyrosine |
| Phenylalanine | Asparagine |
| Tryptophan | Glutamine |
| Methionine | |

Amino Acids with Charged Polar R Groups (negatively charged at Ph 6.0)
Aspartic acid
Glutamic acid
Basic Amino Acids (positively charged at pH 6.0)
Lysine
Arginine
Histidine (at pH 6.0)
Amino Acids with Phenyl Groups
Phenylalanine
Tryptophan
Tyrosine Another grouping may be according to molecular weight (i.e., size of R groups):

| Glycine | 75 | Aspartic acid | 133 |
|---|---|---|---|
| Alanine | 89 | Glutamine | 146 |
| Serine | 105 | Lysine | 146 |
| Proline | 115 | Glutamic acid | 147 |
| Valine | 117 | Methionine | 149 |
| Threonine | 119 | Histidine (at pH 6.0) | 155 |
| Cysteine | 121 | Phenylalanine | 165 |
| Leucine | 131 | Arginine | 174 |
| Isoleucine | 131 | Tyrosine | 181 |
| Asparagine | 132 | Tryptophan | 204 |

Particularly preferred substitutions are:
   Lys for Arg and vice versa such that a positive charge may be maintained;
   Glu for Asp and vice versa such that a negative charge may be maintained;
   Ser for Thr such that a free —OH can be maintained; and
   Gln for Asn such that a free —$NH_2$ can be maintained.

Amino acid substitutions may also be introduced to substitute an amino acid with a particularly preferable property. For example, a Cys may be introduced at a potential site for disulfide bridging with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Purification of the sarA protein from natural or recombinant sources can be accomplished by conventional purification means such as ammonium sulfate precipitation, gel filtration chromatography, ion exchange chromatography, adsorption chromatography, affinity chromatography, chromatofocusing, HPLC, FPLC, and the like. Where appropriate purification steps can be done in batch or in columns.

Peptide fragments of the sar protein can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the subject sar protein.

The present invention also relates to antibodies to the sar protein. Such antibodies may be monoclonal or polyclonal and are contemplated as being useful in developing detection assays (immunoassays) for sar proteins, monitoring sar protein levels and in purifying sar protein. Thus, in accordance with this invention, an antibody to a sar protein encompasses monoclonal or polyclonal antibodies to said sar protein, or to antigenic parts thereof.

Both polyclonal and monoclonal antibodies to the sar protein are obtainable by immunization of an animal with purified sar protein, purified recombinant sar protein, fragments of these proteins, or purified fusion proteins of the sar protein with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual*, Cold Spring Harbor Laboratory, Cold Spring Harbor, N.Y., 726 pp.

Polyclonal sera are relatively easily prepared by injection of a suitable laboratory animal with an effective amount of the purified sar protein, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. (See, for example, Douillard, I. Y. and Hoffman, T., "Basic Facts About Hybridomas", in *Compendium of Immunology*, Vol. II, L. Schwartz (Ed.) (1981); Kohler, G. and Milstein, C., *Nature* 256: 495–497 (1975) and *European Journal of Immunology* 6: 511–519 (1976); Harlow et al.; Koprowski, et al., U.S. Pat. No. 4,172,124; Koprowski et al., U.S. Pat. No. 4,196, 265 and Wands, U.S. Pat. No. 4,271,145, the teachings of which are herein incorporated by reference.

The presence of the sar protein in a sample, such as a culture supernatant and the like, in a microorganism, or in any other source suspected to contain the sar protein, can be detected utilizing antibodies prepared as above, either monoclonal or polyclonal, in virtually any type of immunoassay. Likewise, the present antibodies can be used to identify microorganisms which have or produce sar protein. Accordingly, the present invention provides a method of detecting a sar protein by the steps of contacting a sample suspected of containing said sar protein with an antibody of the invention for a time and under conditions sufficient to form an sar protein-antibody complex and subjecting this complex to a detecting means. As well known to one skilled in the art, the time and conditions for immunodetection assays are variable and depend on the particular assay.

A wide range of detection techniques and conditions are available to one skilled in the art as can be seen by reference to U.S. Pat. Nos. 4,016,043; 4,424,279 and 4,018,653 and to Harlow et al. which provides extensive protocols for immunodetection of molecules. These techniques, of course, include both single-site and two-site, or "sandwich" assays, assays of the non-competitive types as well as competitive binding assays, ELISA, radioimmunoassays, immunoprecipitation and immunoblotting (Western blotting). Sandwich assays are commonly used, a number of variations of the technique exist, and all are intended to be encompassed by the present invention.

Direct and indirect immunoassays, i.e., ELISA, immunoblotting and the like, may employ reporter molecules linked to either a primary antibody (direct assay) or a second antibody or antibody-specific protein such as Protein A or Protein G (indirect assay). The primary antibody can be an antibody of the subject invention labelled with the desired reporter molecule.

By "reporter molecule," as used herein, is meant a molecule which, by its chemical nature, provides an identifiable signal to detect antigen-antibody complexes. Detection may be either qualitative or quantitative. The most commonly used reporter molecules are either enzymes, fluorophores, or radionuclide containing molecules (i.e., radioisotopes). In the case of an enzyme immunoassay, an enzyme is conjugated to the antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase, and alkaline phosphatase among others. The substrate to be used with a particular enzyme is generally chosen for the production of a detectable color change upon reaction. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. After binding an enzyme-labeled antibody to an antigen or antigen-antibody complex, as appropriate, the excess labeled antibody is washed away, and a solution containing the appropriate substrate is added. The substrate reacts with the enzyme, i.e., the reporter molecule, to give a qualitative visual signal or a quantitative signal which can be assessed to indicate the amount of antigen present in the sample.

Alternately, fluorescent compounds, such as fluorescein and rhodamine, may be chemically coupled to antibodies without altering their binding capacity. As used in immunofluorescence, when activated by illumination with light of a specific wavelength, a fluorophore-labeled antibody absorbs the light energy, inducing the fluorophore into an excited stated which is followed by emission of light having a characteristic wavelength. Generally, the emitted light is a characteristic color in the visible range and is detectable with a light microscope equipped for immunofluorescence. Fluorescent antibodies are used in sandwich assays, direct and indirect immunoassays as described above, except after washing, the immune complex is exposed to light of the appropriate wavelength, and the fluorescence is observed. Immunofluorescence and enzyme-based immunoassay techniques are both well established in the art and are particularly preferred. However, other reporter molecules, such as radioisotopes, chemiluminescent or bioluminescent molecules, may also be employed. It will be readily apparent to the skilled technician how to vary the procedure to suit the required purpose.

Another aspect of the invention provides a means of purifying a sar protein by affinity selection. This method involves contacting a sample containing the sar protein with an antibody of the invention, and separating the antigen-antibody complex, e.g., the sar protein-antibody complex from the remainder of the sample and recovering the protein in a form free from the antibody. Typically the complex-containing sample is fractionated and the fraction(s) containing the protein are identified by a convenient biochemical, enzymatic, immunological or other detection means. To facilitate fractionation, the subject antibodies can be bound to a chromatography resin before or after binding to the sar protein. This method can yield purified sar protein in large amounts and in pure form.

Accordingly, the present invention is also directed to a kit for the rapid and convenient assay of a sar protein, in samples suspected of containing the protein. The kit may contain either an antibody directed to the sar protein, and a secondary detectable antibody thereto, or may contain a labelled substrate for the sar protein.

Another aspect of the present invention is directed to a method of detecting the DNA or RNA encoding the subject sar protein by nucleic acid hybridization techniques such as Southern blotting, Northern blotting and the like, or by the polymerase chain reaction (PCR). Accordingly, a method of detecting a sar protein is provided which comprises contacting a sample suspected of containing said sar protein-encoding DNA with a first nucleic acid sufficiently complementary to hybridize to a second nucleic acid which encodes said sar protein in said sample for a time and under conditions sufficient to effect said hybridization and thereby form a complex of said first and second nucleic acids and subjecting said complex to a detecting means. In this method, the first nucleic acid may have a reporter group attached thereto. Reporter groups can include radioisotopes, enzymatically detected groups such as biotin or fluorophores such as rhodamine and fluorescein. Detailed methods for hybridization and blotting is found in Sambrook et al.

For PCR, the present method of detecting a gene encoding the sar protein comprises subjecting a sample suspected of containing the sar gene to a polymerase chain reaction (PCR) using at least two oligonucleotide primers sufficiently complementary to hybridize to a nucleic acid in said sample which encodes said sar protein, and thereby producing at least one amplified nucleic acid segment and identifying said segment. PCR has been described in U.S. Pat. Nos. 4,683,195; 4,683,202; and 4,800,159 which are incorporated herein by reference as well as described extensively in the literature, see for example Saiki et al. (1988), *Science* 239: 487–491. The segment may be detected by gel electrophoresis or blotting, for example.

Also encompassed by the present invention are inhibitors of the sar protein which can be routinely screened using the cleavage assay described above.

Having now generally described this invention, the same will be better understood by references to certain specific examples, which are included herein for purposes of illustration only and are not intended to be limiting of the invention or any embodiment thereof, unless so specified.

EXAMPLE 1 sarA is Necessary for the Optimal Expression of agr
Bacterial Strains, Plasmids and Phage The bacterial strains and plasmids used in this example are listed in Table 1. Phage φ11 was used as a transducing phage for strains RN4220, RN450 and RN6390(3). The following media were used for bacterial growth: CYGP broth for *S. aureus* (15), Luria-Bertani broth (LB) for *E. coli* (13). Antibiotics were used at the following concentrations: ampicillin at 50 μg/ml for *E. coli*, tetracycline at 5 μg/ml and erythromycin at 10 μg/ml for *S. aureus*. Carboxyphenylbenzoyl-aminopenicillanic acid (CBAP) Sigma), an inducer of the β-lactamase promoter in pPN6735, was used at a concentration of 4 μg/ml.

TABLE 1

Bacterial strains and plasmids

| Types | Ref. | Comments |
|---|---|---|
| *A) Bacterial strains* | | |
| *S. aureus* | | |
| DB | (3) | A wild type blood isolate |
| RN450 | (15) | A prototypic strain, which is a derivative of NTCC 8325 cured of prophage, secretes β but not α hemolysin |
| RN6390 | (15) | A laboratory strain that maintains its hemolytics pattern when propagated on sheep red blood cells |
| RN4220 | (15) | A mutant strain 8325-4 that accepts foreign DNA |
| 11D2 | (3) | A mutant derived of DB with a sar::Tn917LTV1 mutation |
| A | this disclosure | As isogenic mutant of RN450 with a sar::Tn917LTV1 mutation |
| R | this disclosure | An isogenic mutant of Rn6390 carrying a sar::Tn917LTV1 mutation |
| RN7372 | (22) | A derivative of mutant A (Tc$^r$) containing pRN6735 and pI524 |
| A35 | this disclosure | A derivative of mutant A (Tc$^r$) carrying two plasmids, pRN6735 and pI524 |
| C7 | this disclosure | A derivative of mutant R (Tc$^r$) containing pRN6735 and pI524 |
| *E. Coli* | | |
| HB01 | (13) | A highly transformable strain |
| *B) Plasmids* | | |
| pALC1 | this disclosure | An *E. coli* plasmid comprising partly of transposon Tn917LTV1 and flanking sar sequence (near the erm-proximal end) was generated by ligating XhoI chromosomal digests of sar mutant 11D2 |
| pALC2 | this disclosure | An *E. coli* plasmid generated by ligating BalI digests of 11D2 - this contains flanking sar sequence distal to the ermproximal end of the transposon |
| pALC3 | this disclosure | pUC18 with a 4 kb chromosomal insert from pALC1 |
| pSPT181 | (10) | A shuttle vector |
| pCRII | | A vector for cloning PCR fragment |
| pALC4 | this disclosure | pSPT181 containing a 732 bp PCR fragment of sarA gene of RN6390 |
| pI524 | (22) | A 30 kb *S. aureus* plasmid encoding the β-lactamase repressor |

TABLE 1-continued

Bacterial strains and plasmids

| Types | Ref. | Comments |
|---|---|---|
| pRN6735 | (22) | A derivative of pC194 (15) containing pI258bla promoter and 2/3 of the blaZ gene followed by the 1,566 bp MboI fragment of RNAIII lacking its promoter |

Cloning and Sequencing Strategies

The transposon Tn917LTV1 inserted into the sar locus of the host chromosome contain an *E. coli* replicon carrying ampicillin as a selective marker (2). Taking advantage of the unique restriction sites (Xho and BalI) within the transposon, ligation mixture of sar mutant 11D2 (3) chromosomal DNA digest were transformed with one of these enzymes into *E. coli* strain HB101. Two plasmid clones (pALC1 and pALC2) comprised partly of transposon and adjacent staphylococcal chromosomal sequences were generated. (Table 1). The plasmid pALC1 was purified (13) and digested with XhoI/SalI to release a 4 kb flanking chromosomal fragment which was then cloned into pUC18 to form the pALC3. The 4 kb insert was subsequently released from PUCII by digestion with SacI/SalI, gel-purified and labeled with $^{32}$P ($\alpha$-$^{32}$P deoxycytidine triphosphate, Amersham) (7) to probe a Zap genomic library (Stratagene, La Jolla, Calif.) of *S. aureus* strain DB as described in the manufacturer's instruction. Two pBluescript phagemids were obtained with inserts of 4.7 and 6 kb, respectively. Plasmids were purified by Magic Maxiprep (Promega, Madison, Wis.). Using both T3 and T7 primers, bidirectional plasmid sequencing was performed with $^{35}$S sequencing mix and Sequenase (US Biochemicals) according to the chain termination method of Sanger (13,19). Additional primers were obtained for sequencing from within the insert. Based on the sequence generated, additional primers were also made to amplify the sar gene by PCR (designated sarA henceforth) from chromosomal DNA of prototypic *S. aureus* strains RN6390 and RN450 (15). The PCR fragment (732 bp) was cloned into pCRII (Invitrogen, San Diego, Calif.), cleaved with XbaI/KpnI, and re-cloned into shuttle vector pSPT 1818 110) in *E. coli* strain XL-1 blue.

Shuttle plasmid pSPT181 carrying the cloned sarA gene (designated pALC4) from strain RN6390 was transformed into RN4220 by protoplast transformation (3) to select for Tc$^r$ colonies at 32° C. Aφ11 lysate of a RN4220 Tc$^r$ transformant, which has been verified to carry the reconstructed plasmid pALC4 by restriction analysis (3), was prepared and used to infect sar mutants R and A (derived from RN6390 and RN450, respectively) to obtain Tc$^r$ Erm$^r$ transductants. Positive transductants were verified by restriction analysis.

To verify that the cloned sarA gene is responsible for the production of selected hemolysins in the complemented sar mutants, α, β and δ hemolysin production was assayed on plain and cross streaked sheep and rabbit erythrocyte agar using specific indicator strains as standards as previously described (17). This confirmed the restoration of α- and β-hemolysin production in mutants R and A, respectively, upon the introduction of the plasmid pALC4 (Table 2). Using the culture supernatants of RN6390 and mutant R as the respective positive and negative controls, verified the secretion of hemolysin in complemented mutant R by probing the culture supernatant of this strain with affinity-purified anti-α hemolysin antibody in an immunoblot as previously described (4).

To evaluate the effect of a sar mutation on RNAIII (the agr regulatory molecule), bacterial RNA was prepared from two pairs of isogenic *S. aureus* strains (RN450 and RN6390 together with their sar mutants) and their corresponding complemented mutants using a method described by Kornblum et al (12). For Northern blots, equal volumes (≈7.5 μl) of samples extracted from equivalent number of bacterial cells at late log phase were electrophoresed through a 1.5% agarose-0.66 M formaldehyde gel in MOPS running buffer (20 mM MOPS, 10 mM sodium acetate, 2 mM EDTA, pH 7.0) (13). RNA was transferred onto Hybond N membrane (Amersham) according to manufacture's instruction and allowed to hybridize in 50% formamide at 42° C. overnight with a $^{32}$P labeled (random-primed) gel-purified RNAIII probes (1.5 kb MboI fragment of pRN6735—Table 1) (13). Following hybridization, the membrane was washed twice in 2× SSC with 0.1% SDS at RT for 10 min. each, once with 1× SSC with 0.1% SDS at 55° C. for 15 min, and finally autoradiographed.

Figure 1B:
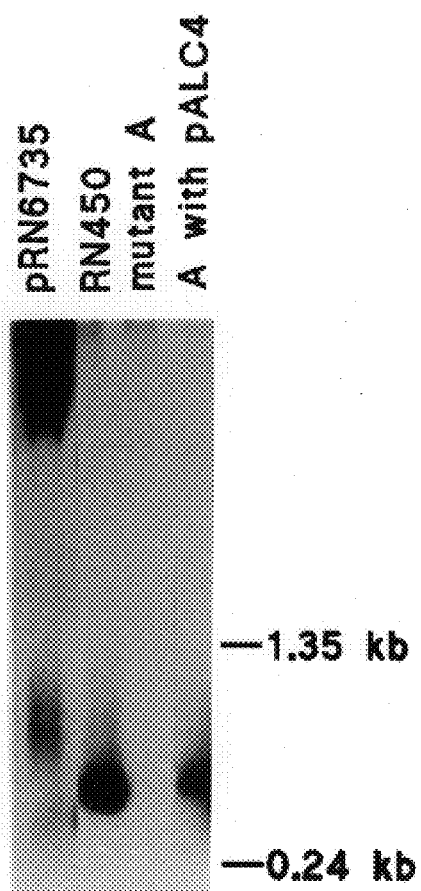

As shown in FIG. 1, the levels of RNAIII in mutants A and R were either absent or significantly diminished as compared to the parents. However, mutants A and R transformed with the shuttle plasmid, pALC4, which carried an intact sarA gene (from RN6390) as confirmed by a Northern blot with a sarA probe, were able to partially restore RNAIII levels to that of the parents (FIG. 1).

If sarA is assumed to be a positive regulator of agr, one would expect complementation of selected sar phenotypes with a plasmid carrying RNAIII (i.e. pRN6735—see Table 1). As the cloned RNAIII fragment in pRN6735 was under the control of a β-lactamase promotor that was normally repressed in the presence of pI524 (22), the production of RNAIII in mutant A was low at the basal level but was highly inducible by the addition of a β-lactam compound such as carboxyphenylbenzoyl-aminopenicillanic acid (CBAP). Using this approach, it was found that the production of β hemolysin in the complemented mutant A35 was reestablished as compared with sar mutant A. Similarly, the production of β-hemolysin which was not detected in mutant A was weakly expressed in the complemented mutant (Table 2).

TABLE 2

Complementation of α and β hemolysin expression in sar mutants

| Strains | α hemolysin | β hemolysin | δ hemolysin |
|---|---|---|---|
| RN450 | − | ++ | +/− |
| A | − | − | − |
| A with pALC4 | − | ++ | +/− |
| A35 (no CBAP) | − | ++ | +/− |
| A35 (CBAP | − | ++ | +/− |
| RN390 | + | ++ | + |
| R | − | − | − |
| R with pALC4 | + | ++ | ++ |

EXAMPLE 2

Sequence Analysis of sarA Gene

Using a 732 bp cloned sarA gene as a probe, Southern blot hybridization of chromosomal DNA digested with EcoRI (internal to the structural gene), HindIII and EcoRV (external to sarA) revealed one copy of this gene in three *S. aureus* strains, DB, RN450 and RN6390. Of these, the complete sarA gene of strains DB and RN450 was sequenced. Sequence analysis and comparisons with known databases were conducted with the Sequence Analysis Software Package for the Genetics Computer Group (GCG package, University of Wisconsin, Madison, Wis.) (5). Sequence data revealed identical sarA sequences between the two strains. By sequencing plasmids (pALC2 and pALC3) comprised partly of transposon and flanking chromosomal sequences, site of the transposon Tn917LTV1 was located to 5 bp downstream from the translation start in strain DB (FIG. 2). The sarA gene has an open reading frame of 372 bp. The sequence has a GC content (27%) similar that found in the staphylococcal genome (30%) (6). A putative ribosomal binding site (underlined) is indicated in FIG. 2. The mature protein has a predicted molecular size of 14,718 Da with a deduced basic pI of 8.52. The deduced protein has a predominance of charges residues (33%). Four major residues constitute ≈44% of its composition-lysine (12.9%), glutamic acid (11.2%), leucine (10.4%) and isoleucine (9.6%). In addition, there is an absence of glycine and tryptophan residues. Garnier analysis of the deduced amino acid sequence suggested that the molecule is primarily α helical (77%) (5). Additional conformational analysis with the GCG package indicated that a helix-turn-helix motif is not apparent in the deduced sequence. It also does not appear to have significant similarity with sequence elements of the two-component signal transduction system that are located in the C-terminal domain of the signaling component and in the N-terminal domain of the activator component (14). Comparison of this protein sequence with others in the Genbank database revealed similarity to virF gene of *Shigella flexneri* (18) (FIG. 2).

EXAMPLE 3

Further Sequence Analysis

In the experiments in this example, we reported and analyzed the nucleotide sequence of sarA of strain RN6390, the upstream sequence of sarA and the termination signal downstream of sar. In analyzing the transcriptional organization of the sar locus, we present data that three overlapping transcriptional units originate from the sar locus and are controlled in a temporal manner by a parallel multiple promoter system. In addition, we demonstrated that the expression of the overlapping transcriptional sar units was required to restore parental phenotypes to the sar mutant.

MATERIALS AND METHODS

Bacterial strains, plasmids, and growth media. The bacterial strains and plasmids used in this study are listed in Table 3. Phage φ11 was used as the transducing phage for *S. aureus* strains. CYGP and 0.3GL media (41) were used for the growth of *S. aureus* while Luria-Bertani broth (LB) was used for growing *E. coli*. Antibiotics were used at the following concentrations: erythromycin at 10/μg/ml, tetracycline at 5/μg/ml, and ampicillin at 50/μg/ml.

TABLE 3

Bacterial strains and plasmids

| Strain or Plasmid | Refs. | Comments |
|---|---|---|
| *S. aureus* | | |
| RN4220 | (40) | A mutant of strain 8325-4 that accepts foreign DNA |
| RN6390 | (40) | Laboratory strain that maintains its hemolytic pattern when propagated on sheep erythrocytes |
| ALC136 | (4) | Isogenic mutant of RN6390 carrying a sar::Tn917LTV1 mutation |
| ALC103 | (34) | ALC 136 with pALC103 |
| ALC556 | This work | ALC136 with pALC556 |
| ALC557 | This work | ALC136 with pALC557 |
| ALC561 | This work | ALC 1 36 with pALC561 |
| ALC529 | This work | ALC136 with pALC529 |
| *E. coli* | | |
| XL1 -Blue | (13) | Highly transformable strain |
| InvαF' | Invitrogen | Host strain for the TA cloning vector (PCRII) |
| Plasmids | | |
| PCRII | Invitrogen | *E. coli* cloning vector for direct cloning of PCR fragments |
| pSPT181 | (10) | Shuttle vector |
| pALC103 | (34) | pSPT181 with sar fragment nt 620-1349 |
| pALC556 | This work | pSPT181 with sar fragment nt 531-1349 |
| pALC557 | This work | pSPT181 with sar fragment nt 364-1349 |
| pALC561 | This work | pSPT181 with sar fragment nt 1-1349 |
| pALC529 | This work | pSPT181 with sar fragment nt 1-1231 and additional 300 bp upstream sequence |

Sequence analysis. A pBluescript phagemid with a 6 kb insert encompassing the sar locus was used. Plasmids were purified by the Magic Midiprep procedure (Promega, Madison, Wis.). Using both T3 and T7 primers, bidirectional plasmid sequencing was performed and completed by primer walking with the Sequenase-kit version 2.0 (US Biochemicals, Cleveland, Ohio) according to the dideoxy chain termination method.

Construction of 5' and 3' deletion clones. DNA fragments of the sar locus at several positions (FIG. 3), 1–1349, 364–1349, 531–1349, and 1–1231 with additional 300 bp upstream sequence, were amplified by PCR using genomic DNA of *S. aureus* strain RN6390 as the template, and cloned into the TA cloning vector PCRII (Invitrogen, San Diego, Calif.). The authenticity of the amplified fragments was confirmed by DNA sequencing. The PCR fragments were cleaved from PCRII, ligated to the shuttle vector pSPT181, and transformed into *E. coli* XL1-Blue. The presence of the correct inserts in the plasmids was confirmed by restriction mapping and sequencing.

Protoplast transformation of *S. aureus* strain RN4220 with shuttle plasmids containing various sar fragments was performed as previously described (27). For transduction, phage φ11 was used to produce a phage lysate of strain RN4220 containing the modified pSPT181 shuttle vector with various sar DNA fragments. The phage lysate was then used to infect the sar transposon mutant (ALC136—previously designated as mutant R) as described (3), producing ALC561, ALC557, ALC556, and ALC529, respectively (Table 3).

Phenotypic characterization. A sar mutant clone carrying a shuttle plasmid with a sar fragment was tested in duplicate for the production of hemolysins as previously described (3). To determine levels of protein A production, cell wall-associated proteins were extracted from overnight cultures of *S. aureus* with lysostaphin in a hypertonic medium (30% raffinose) as previously described (30). Equivalent volumes (1 μl each) of cell wall-protein extracts were separated on 10% sodium dodecyl sulfate-polyacrylamide gels, electroblotted onto nitrocellulose and probed with chicken anti-staphylococcal protein A antibody (Accurate Chemicals, Westbury, N.Y.) at a 1:3000 dilution. Bound antibody was detected with rabbit anti-chicken IgG conjugated to alkaline phosphatase (Jackson Immunoresearch, West Grove, Pa.) (1:5000 dilution) and visualized as described by Blake et al. (23).

The ability of whole cells to bind to $^{125}$I-labeled fibronectin was assayed as described (29). The Student t test was used to compare the binding of radiolabeled fibronectin to parental and sar mutant strains. P values ≦0.05 were considered significant.

Isolation of RNA and northern analysis. Overnight cultures of *S. aureus* were diluted 1:100 in CYPG, and grown to early-, mid-, late-log and post-exponential phases. The cells were pelleted and processed with the FastRNA isolation kit (BI0101, Vista, Calif.) in combination with 0.1 mm Zirconia/Silica beads and a FastPrep reciprocating shaker (Biol 01) as described previously (28). Ten μg of each sample was electrophoresed through a 1.5% agarose-0.66 M formaldehyde gel in MOPS running buffer (20 mM MOPS, 10 mM sodium acetate, 2 mM EDTA, pH 7.0). Blotting of RNA onto Hybond N membrane (Amersham, Arlington Heights, Ill.) was performed using the Turbo Blotter Alkaline Transfer System (Schleicher and Schuell, Keene, N.H.). For detection of specific transcripts, DNA probes were radiolabeled with $\alpha^{32}$P-dCTP (Amersham) by the random prime method (Ready to Go Labeling Kit, Pharmacia, Piscataway N.J.) and hybridized under high stringency conditions. The blots were subsequently autoradiographed.

Primer extension analysis. Mapping of the 5' ends of the sar transcripts A, B and C by primer extension was performed with a series of synthesized oligonucleotides complementary to both DNA strands, respectively. The 23mer primers used in FIG. 6A–C correspond to the complementary strand of the sequence given in FIG. 3 as follows: 5'-TAAGTGACCATTGATAACAACTC-3' (position 918-896); SEQ ID NO: 1, 5'-TGTTTCGATATTCAATGTGTGTC-3' (position 525-503); SEQ ID NO: 2, 5'-TGTCTATACGTTATTCCGATTGA-3' (position 309-287); SEQ ID NO: 3, respectively. The primers were end-labeled with $\gamma^{32}$P-ATP and purified by Sephadex G25 spin columns (Boehringer Mannheim, Indianapolis Ind.).

For primer extension, 30 μg of RNA was co-precipitated with the appropriate end-labeled primer (5×10$^4$ cpm) and then annealed at 35° C. overnight. The reaction mixture was ethanol precipitated, washed with 70% ethanol and dried. Reverse transcription was carried out using SuperScriptII (Gibco-BRL, Gaithersburg Md.) at 42° C. for 90 min and heated at 65° C. for 10 min to inactivate the enzyme. The reaction product was incubated with RNase H (2 units) for 15 min at 55° C., ethanol precipitated, resuspended in 10 μl of Sequenase stop solution, denatured and applied onto a 4% sequencing gel. Sequencing reactions primed by an identical oligonucleotide used for primer extension were applied in parallel lanes on the gel.

Mapping of transcriptional start and stop sites. Mapping of the 5' and 3' ends of different sar mRNAs was performed with several single stranded riboprobes complementary to the appropriate sequence of the transcripts. All probes were tested on sequencing gels for their integrity prior to S1 analysis.

To generate the 3'-riboprobe, a 358 bp fragment (position 992-1349) covering—200 bp of the 3' end of the sar encoded sequence plus a 160 bp downstream fragment including the putative transcription termination signal, was amplified by PCR using the primer 5'-ATCAGCGAAAACAAAGAGAAAGAAT-3' (position 992-1016) SEQ ID NO: 4 and 5'-AGTGCCATTAGTGCAAAAC-3' (position 1349-1331) SEQ ID NO: 3. The PCR product was cloned into PCRII, transformed to XL1-blue and sequenced to determine the orientation of the insert. Using this modified PCRII vector as a template, a second PCR was performed with the vector-specific M13 Reverse Primer and a sar specific primer identical to position 992-1016, thus generating a PCR product that carries a SP6 phage promotor in front of the sar specific probe encompassing the 3' end. SP6 driven in vitro transcription of a single stranded probe complementary to the 3' end of the mRNA was performed using a standard transcription assay (MAXIscript SP6/T7, Ambion, Austin, Tex.). To ensure the synthesis of a full length probe, the radiolabeled $\alpha^{32}$P-UTP was supplemented with cold UTP to a final concentration of 7.5 $\mu$M. The reaction was incubated at 16° C. for 2 hrs followed by RNase-free DNaseI treatment at 37° C. for 15 min.

In an additional approach to map the 5' ends of different sarmRNAs, we followed a similar procedure to generate single stranded 5'-riboprobes. Specific DNA fragments of approximately 350 bp in length encompassing the putative 5' end of various transcripts were used as templates for PCR amplification. After cloning the PCR fragments into PCRII, the inserts were subjected to a second PCR with a T7 phage promoter specific primer, thus generating a T7 phage promoter in front of the sar probe. In vitro transcription for the synthesis of full length antisense RNA probes was allowed to proceed at 10° C. for 3 hrs.

The specific activity of probes generated this way usually ranged between 2 and 8×10$^7$ cpm/$\mu$g DNA template.

Modified S1 nuclease protection assay. Ten $\mu$g of RNA was mixed with 10$^5$ cpm of riboprobe, heated to 85° C. for 3 min and then incubated in hybridization buffer (40 mM PIPES, pH 6.4, 400 mM NaCl, 1 mM EDTA, 80% (w/v) formamide) at 42° C. overnight. Digestion of unprotected fragments was performed in 30 mM NaOAc pH 4.8, 10 mM ZnSO$_4$, 5% glycerol, 100 mM NaCl and 60 units of S1 nuclease at 37° C. for 30 min. After ethanol precipitation, the protected RNA hybrids were resuspended in water and gel loading buffer, heat denatured and run on a 4% sequencing gel. For the exact determination of the 3' and 5' ends of mRNA, a concomitant sequencing reaction using a primer identical to the ones used for the generation of riboprobes, was applied onto parallel lanes and subsequently autoradiographed.

Computer analysis. Sequence analysis was performed with the Wisconsin Genetics Computer Group, Inc., package. For the prediction of prokaryotic termination signals we used the program TERMINATOR (25, 26) from the HUSAR package of the DFKZ Heidelberg, Germany.

Nucleotide sequence accession number. The nucleotide sequence reported here is available from GenBank under the accession number U46541.

RESULTS

In previous studies, we identified the sar locus as a global regulator of several virulence determinants in *S. aureus* (3, 4, 29). In particular, the sar locus may regulate hemolysin production by controlling RNAII and RNAIII transcription in the agr locus (31,34). Recently, we found that the sarA gene together with a 1.2 kb upstream fragment was required to complement agr-related transcription in a sar mutant (34). To determine the genetic requirements for sar function and transcription, we sequenced and analyzed the sarA gene in strain RN6390 and the region upstream.

Sequence analysis of sarA and the upstream region. The nucleotide sequence of the 1.35 kb fragment encompassing sarA is given in FIG. 3. The ORF encoding the sarA gene begins at position 866 with a start codon and extends to position 1204 followed by a stop codon. A highly conserved Shine-Dalgarno sequence is centered 11 bp upstream of the initiation codon. Within the sarA gene two 10 bp direct repeats are located at positions 927 and 940 (FIG. 4A). The mature protein has a predicted molecular size of 13,469 Da and a deduced basic pI of 9.37. With the exception of a slightly truncated C-terminus and a conservative substitution at residue 53 in which a leucine is exchanged for phenylalanine, this sarA protein is highly homologous to that of strains RN450 and DB (FIG. 4B) (32). As with the sarA protein for strain RN450, this protein also has a preponderance of charged amino acids (34.3%).

Examination of the 865 bp DNA sequence upstream of sarA indicates that this region contains no additional large ORF. To exclude possible sequencing errors, both strands have been sequenced several times by both the dideoxy chain termination protocol and ABI dye termination fluorescence-based cycle sequencing. A computer analysis using the programs TESTCODE and CODONPREFERENCE revealed neither a pattern of alternating ORFs located on different frames nor an extended sarA coding region. However, two additional small polypeptide encoding ORFs (see FIG. 3) located at position 599 to 715 (ORF3 encoding 39 aa—see FIG. 9) and at position 243 to 296 (ORF4 encoding 18 aa), respectively, could be detected. The region immediately upstream of ORF 3 is defined by a putative but weakly conserved ribosome binding site 11 bp upstream of a possible initiation codon, followed by a biased G/C rich 2nd codon and A/T rich stretch in the third and fourth codon, and an A at position −3, in compliance with the rules obtained from translational initiation sites in *E. coli*. Interestingly, this RBS is part of an inverted repeat whose axis of symmetry lies 26 bp upstream of the initiation codon of ORF3. In contrast, no obvious Shine-Dalgarno sequence could be identified upstream of ORF 4, nor does this region encompass any of the known required features for translation.

Transcriptional analysis of the sar locus. Northern blot analysis of the sar transcripts with several DNA probes representing various segments of sarA (probes 2–5 in FIG. 5) as well as the entire sar locus (probe 1) revealed three transcriptional units sizing at 0.58, 0.8, and 1.15 kb, respectively. In a previous study (11), we hypothesized the 0.8 kb transcript to be a degradation product based on its weak hybridization signal in a northern blot using log phase cultures. However, subsequent probe walking using only selected upstream probes (probes 6 and 7) resulted in abolition of first the 0.58 kb transcript and then the 0.8 kb transcript, suggesting three different sites of transcriptional initiation. Probes complementary to sequences either further upstream of probe 7 or downstream of probe 2 were not able to detect any of the above transcripts (not shown).

Figure 7:
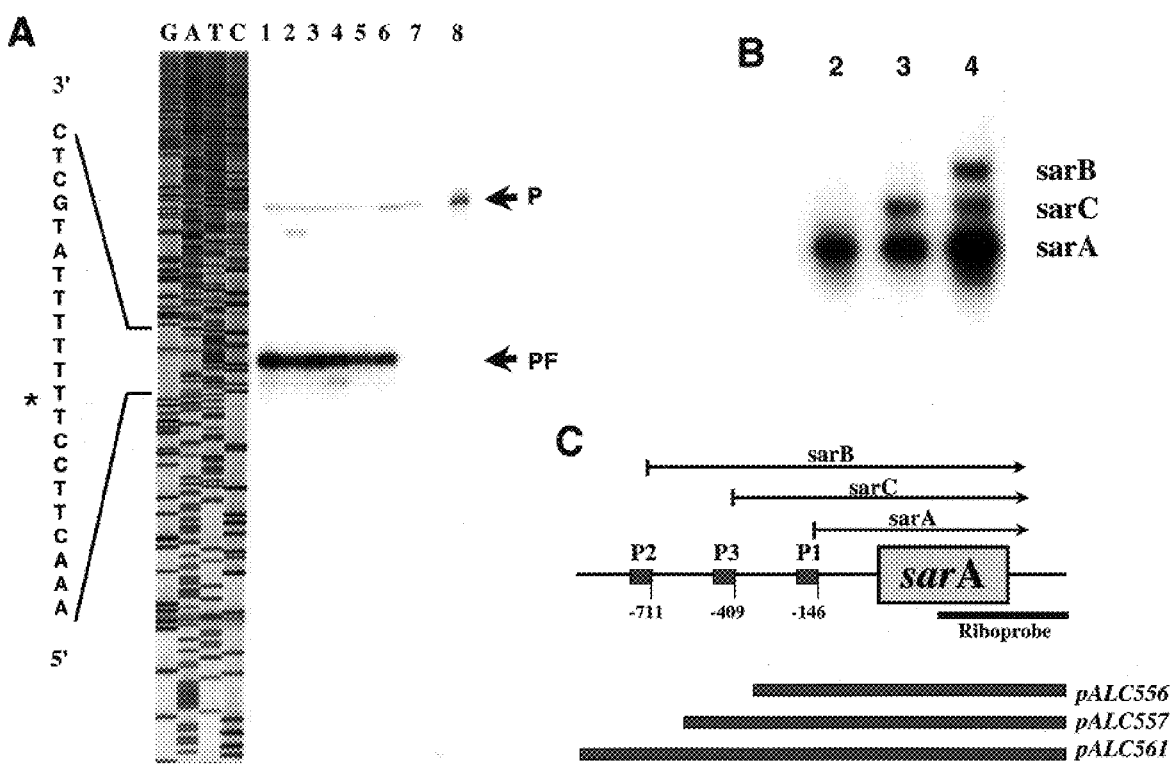
FIG. 7. 3' mapping of the sar transcripts. (A) [SEQ ID NO.: 17] S1 nuclease protection assay. A concomitant sequencing reaction with a primer identical to the 5' end of the riboprobe was run in parallel lanes. The termination region is outlined on the left with the exact 3' end indicated by a star. Protected fragments (PF) of the wild type RN6390 from early, mid, and late log-phase cells (lane 1, 5, and 6, respectively), the 5' deleted clones ALC556 (lane 2), ALC557 (lane 3), ALC561 (lane 4), a reaction of riboprobe (R) and S1 nuclease without RNA (lane 7), and the riboprobe alone (lane 8) were applied onto a sequencing gel. (B) Transcriptional analysis of 5' deletion clones. RNA from cells grown to late log phase was prepared as described in materials and methods. Northern analysis of clones encompassing the promoters P1 (ALC556), P1 and P3 (ALC557), or P1, P3 and P2 (ALC561), as predicted by the primer extension data, was performed with a DNA probe encompassing the entire sarA coding region. (C) Physical map of the sar region. The riboprobe used in the S1 nuclease mapping is indicated by a solid line. Various 5' deletion sar clones are represented by dark bars. Promoter positions are labeled P1, P2, and P3, respectively. The arrows depict the sar transcripts. The distances between the 5' ends of the transcripts and the start codon of sarA are expressed by negative position numbers.

To verify this model of transcriptional initiation, we mapped the 5' ends of all three sar transcripts by primer extension, walking in 200–300 bp increments along both strands of the entire 1.3 kb region. Only three primer extension products derived from the sarA coding strand could be detected (FIGS. 3 and 6) with the transcription start sites positioned at 720, 457, and 155 (designated P1 at −146, P3 at −409, and P2 at −711 relative to the sarA start codon in FIG. 7). This finding also excludes the possibility of overlapping transcripts derived from the DNA strand complementary to the one listed in FIG. 3. To confirm the primer extension data, a second mapping approach with a modified S1 nuclease protection assay involving single stranded riboprobes was performed. The S1 mapping data were in complete concordance with those of the primer extension (data not shown). The transcription initiation sites of the three sar transcripts together with the putative −10 and −35 promoter boxes as well as with other regulatory regions are shown in FIG. 3 with analysis given in the discussion.

Mapping of the termination signal salt. To demonstrate that all three sar transcripts possess the very same termination signal recognized by the RNA polymerase, a S1 nuclease mapping of the 3'-ends of the sar transcripts was performed. We carried out a computer analysis of the downstream region of sarA to facilitate the construction of an appropriate mapping probe. The program TERMINATOR (25) which searched for prokaryotic RNA polymerase-terminators independent of rho-factors, predicted a constitutive termination site at position 1301 (p=3.88) by applying a normalized dinucleotide distribution matrix (p=>3.5) alone. Using a combined search based on an additional complementarity weight matrix (degree of dyad symmetry), no higher score could be obtained. This is not surprising because an inspection of the sequence revealed a profound 26 bp hairpin structure formed at position 1262 to 1295 (see FIG. 3), with the center of the hairpin lying between positions −23 and −24 (with the predicted termination site as position −1) and a loop size of 8 bp, thus being 1 nt too long to meet the criteria of Brendel (25), even though all other parameters fit quite well.

The S1 nuclease assays were performed with single stranded RNA probes generated by in vitro transcription. These probes derived from clones carrying the appropriate DNA fragment downstream of a SP6 promoter. For this experiment, we used the wild type strain showing the regular transcription pattern and sar transposon mutants carrying shuttle vectors with various 5'-deleted regions of the sar locus (FIG. 7C) to initiate transcription at either P1 alone, P1 and P3, or P1-P3-P2, respectively (FIG. 7B). As indicated, all sar transcripts terminated at exactly the same position at nt 1298 (FIG. 7A), thus encoding the complete C-terminus of sarA. This is in close vicinity to the putative termination site as predicted by computer analysis. Furthermore, northern analysis of the derivative clone ALC529 lacking this signal resulted in readthrough transcription into the vector (data not shown).

Phenotypic characterization. Based on our primer extension data, we wanted to determined if the deficiency in sar-related functions in a sar mutant can be complemented by a plasmid carrying the 1349 bp fragment that encodes all three sar transcripts. This fragment was successfully introduced into sar mutant ALC136 via a shuttle vector to yield sar mutant clone ALC561. Phenotypic analysis of this clone (ALC561) demonstrated that this sar fragment was able to restore parental functions to the sar mutant (Table 4). For instance, levels of α and β hemolysin production, which were reduced in the sar mutant ALC136, were restored to nearly parental levels in this clone. Immunoblot analysis revealed that a low level of protein A was produced by the parental strain (RN6390) but was up-regulated in the sar mutant ALCL 36. As anticipated, protein A production returned to parental levels in the sar mutant clone containing the plasmid with the 1349 bp sar fragment. The binding of whole cells to $^{125}$I-labeled fibronectin was slightly diminished in sar mutant ALCL 36 when compared to parental strain RN6390. However, complementation of the sar mutant with the sar fragment encompassing all three sar-related transcripts (ALC561) produced a dramatic increase in fibronectin binding (Table 4). In contrast, the transposon mutant complemented with sarA alone (ALC103), did not exhibit a similar increase in fibronectin-binding capacity (data not shown).

TABLE 4

Phenotypic characterization of an sar mutant clone encompassing the sar locus

| | RN6390 | ALC136 | ALC561 |
|---|---|---|---|
| α hemolysin* | + | − | + |
| δ hemolysin* | + | − | + |
| Fibronectin binding protein† | 3320 ± 503 | 2393 ± 124 | 19288 ± 2295 |

*These were assayed by measuring the zones of hemolysis on cross-streaked rabbit erythrocyte agar plates.
+: moderate producer;
−: non-producer.
†Data presented as cpm of $^{125}$I fibronectin bound to $10^9$ CFU ± SEM.

Figure 8:
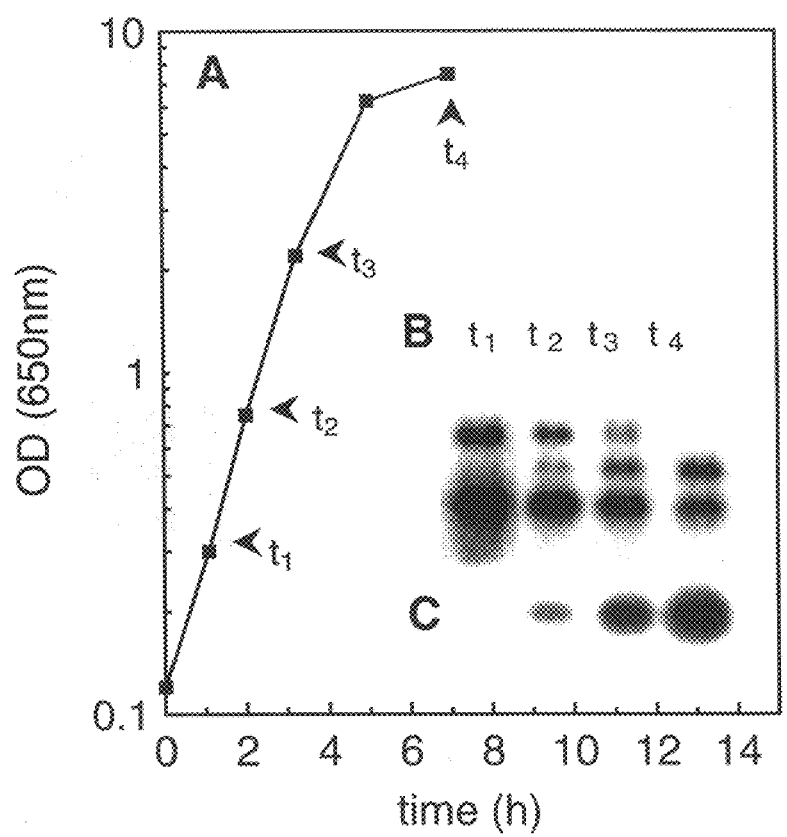
FIG. 8. Growth cycle dependent regulation of the sar transcripts. (A) Growth of *S. aureus* strain RN6390. Time points at which RNA has been prepared for northern analysis are indicated by arrows. Northern analysis of the sar transcripts (B) and the RNAIII transcript of the agr locus (C) with PCR-generated probes derived from positions 620–1349 (FIG. 3) and 555–1773 (19), respectively.

Growth cycle dependency of sar. S. aureus RNA harvested at various time points during the growth cycle at early log-, mid log-, late log-, and stationary phases revealed a temporal dependency of all three sar transcripts (FIG. 8). Wherein the concentration of sarB and the more abundant sarA transcripts tapered during the late growth cycle, the sarC transcription unit began to appear during the log phase and increased in the late stationary phase (FIG. 8B). In contrast, the expression of RNAIII displayed the expected increase in transcription towards the stationary phase as shown in FIG. 8C, clearly demonstrating a delay in expression as compared to sar.

Production of cell-free extracts and gel shift analysis. Cell-free extracts were prepared from strain RN6390 and the isogenic sar transposon mutant (ALC136) as well as the mutant complemented with the plasmid pSPT181 carrying various PCR-generated sar fragments. Cells were grown overnight in 200 ml of CYGP broth supplemented with the appropriate antibiotics. After pelleting, the cells were resuspended in 1 ml of TEG buffer (25 mM Tris, 5 mM EGTA, pH 8) and cell-free extracts were prepared from lysostaphin-treated cells as described by Mahmood and Khan (J. Biol. Chem. 265:4652–4656, 1990).

For the gel shift assay, varying volumes of cell-free extracts were added to reaction mixtures containing 10 mM Tris HCl, pH 7.5 with EDTA (1 mM), dithiothreitol (1 mM), NaCl (50 mM), glycerol (5%), and 1 μg of poly (dI-dC) to a final vol of 25 μl. Approximately 1–2×10$^4$ cpm of the $^{32}$P end-labeled P2 or P3 promoter probe was then added. To evaluate the role of the peptide encoded by ORF3 (see FIG. 9), we added synthetic peptides (0.1–1 μg) corresponding to ORF3 in some gel shift assays. In some assays, unlabeled P2 promoter DNA was used as a specific competitor while a 210 bp fragment upstream of the sar locus or a 163 bp PCR fragment of the α-hemolysin gene was used as a non-specific competitor. The reaction mixtures were incubated at room temperature for 5 min and then on ice for an additional 5 min, and then electrophoresed on a 6% polyacrylamide gel in 0.25× TBE for 2 h at 200 V. Following electrophoresis, the gels were dried and exposed to film.

Results: Retardation of the P2 promoter fragment of agr occurred with the cell-free extract of parent strain RN6390 but not with that of the isogenic sar mutant (ALC136). Surprisingly, the addition of the peptide encoded by ORF3 interfered with the ability of the cell-free extract of parental strain RN6390 to bind to the P2 promoter fragment. Similarly, cell-free extract of a sar mutant clone containing a shuttle plasmid with all three sar transcriptional units altered the mobility of a P2 promoter fragment but this binding activity was reduced in the presence of the peptide encoded by ORF3. These data suggest that the peptide encoded by ORF3 binds to the sarA protein, thereby interfering with its ability to bind to the agr promoter region.

Cloning strategies. DNA fragments containing regions of the sar locus of *Staphylococcus epidermidis* were amplified by PCR using genomic DNA of *Staphylococcus epidermidis* strain within the Rockefeller University Strain Collection as a template. The fragment was cloned into the TA cloning vector pCRII (Invitrogen, San Diego, Calif.). The sequence of the amplified fragments was obtained by sequencing with $^{35}$S sequencing mix and Sequenase (US Biochemicals, Cleveland, Ohio) with a primer-walking technique (13).

Computer analysis. Sequence analysis was performed with the Wisconsin Genetics Computer Group, Inc., package. For the prediction of prokaryotic termination signals we used the program TERMINATOR from the HUSAR package of the DFKZ Heidelberg, Germany.

Phenotypic characterization. An *S. aureus* sar mutant clone carrying a shuttle plasmid with a sarA fragment of *S. epidernidis* was tested in duplicate for the production of hemolysins as previously described (20). To determine levels of protein A production, cell wall-associated proteins were extracted from overnight cultures of *S. aureus* with lysostaphin in a hypertonic medium (30% raffinose) as previously described. Equivalent volumes (1 μl each) of cell wall-protein extracts were separated on 10% sodium dodecyl sulfate-polyacrylamide gels, electroblotted onto nitrocellulose and probed with chicken anti-staphylococcal protein A antibody (Accurate Chemicals, Westbury, N.Y.) at a 1:3000 dilution. Bound antibody was detected with rabbit anti-chicken IgG conjugated to alkaline phosphatase (Jackson Immunoresearch, West Grove, Pa.) (1:5000 dilution) and visualized as described by Blake et al. (*Anal. Biochem*. 136:175–179, 1984)

Results: In comparing the two sarA proteins between *Staphylococcus aureus* and *Staphylococcus epidermidis*, it was evident that the two sarA proteins are highly homologous (see FIG. 10). They have similar molecular weight with a basic pI of 8.5. Alignment of the two protein sequences uncovered 85% identity. For those amino acids that are not identical, 59% contained conservative substitution. In additional experiments, the sarA homolog of *S. epidermidis* was cloned into a shuttle plasmid (pSPT181) and introduced into a *S. aureus* sar mutant. Remarkably, this gene was able to complement the sar-related deficiency in the mutant as if it behaved like a sarA gene of *S. aureus* (i.e., activating hemolysin production and suppressing protein A production). Thus, the sarA gene is both structurally and functionally conserved between these two staphylococcal species.

While the invention has been described and illustrated herein by reference to various specific materials, procedures, and examples, it is understood that the invention is not restricted to the particular materials, combinations of materials, and procedures selected for that purpose. Numerous variations of such details can be implied and will be appreciated by those skilled in the art.

REFERENCES

1. Brennan, R. G. et al. 1989. The helix-turn-helix binding motif. *J. Biol. Chem*. 264:1903–1906.
2. Camilli, A., et al. 1990. Insertional mutagenesis of *Listelia monocytogenes* with a novel Tn917 derivative that allows direct cloning of DNA flanking transposon insertions. *J. Bacteriol*. 172:3738–3744.
3. Cheung, A. L., et al. 1992. Regulation of exoprotein expression in *Staphyloccus aureus* by a locus (sar) distinct from agr. *Proc. Natl. Acad. Sci. USA*. 89:6462–6466.
4. Cheung, A. et al. 1994. Regulation of α and β hemolysins by the sar locus of *S. aureus, J. Bacteriol*., 176:580–585.
5. Devereux, J. P. et al. 1984. A comprehensive set of analysis programs for the VAX. *Nucl. Acids Res*. 12:387–395.
6. Easmon, C. S. F. et al. 1983. Staphylococci and staphylococcal infections, Academic Press, New York.
7. Feinberg, A. P. et al. 1983. A technique for radiolabeling DNA restriction endonuclease fragments to high specific activity. *Anal. Biochem*. 132:6–13.
8. Hale, T. L. 1991. Genetic basis of virulence in Shigella species. *Microbiol. Rev*. 55:206–224.
9. Hart, M. E., et al. 1993. The extracellular protein regulator (xpr) affects exoprotein and agr mRNA levels in *Staphylococcus aureus. J. Bacteriol*. 175:7875–7879.
10. Janzon, L. et al. 1990. The role of the δ-hemolysin gene (hld) in the regulation of virulence genes by the accessory gene regulator (agr) in *Staphylococcus aureus, EMBO. J*., 9:1391–1399.
11. Kornblum, J., et al. 1990. Agr: A polycistronic locus regulating exoprotein synthesis in *Staphylococcus aureus*, p.373–402. In R. P. Novick (ed.), Molecular biology of the staphylococci, VCH Publishers, New York.
12. Kormblum, J. et al. 1988. A rapid method to quantitate non-labeled RNA species in bacterial cells. *Gene* 63:75–85.
13. Maniatis, T., et al. 1989. Molecular cloning, a laboratory manual, Cold Spring Harbor Laboratory, Cold Spring Harbor, N.Y.
14. Nixon, B. T., et al. 1986. Two component regulatory systems responsive to environmental stimuli share strongly conserved domains with the nitrogen assimilation regulatory genes ntrB and btrC. *Proc. Natl. Acad. Sci. USA*. 83:7850–7854.
15. Novick, R. P. 1991. Genetic systems in staphylococci. *Methods Enzymol*. 204:587–636.
16. Novick, R. P., et al. 1993. Synthesis of staphylococcal virulence factors is controlled by a regulatory RNA molecule. *EMBO. J*. 12:3967–3977.
17. Rescei, P., et al. 1986. Regulation of exoprotein gene expression in *Staphylococcus aureus* by agr. *Mol. Gen. Genet*. 202:58–61.
18. Sakai, T., et al. 1986. DNA sequence and product analysis of the virF locus responsible for congo red bindling and cell invasion in *Shigella flexneri* 2a. *Infect. Immun*. 54:395–402.
19. Sanger, F., et al. 1977. DNA sequencing with chain terminating inhibitors. *Proc. Natl. Acad. Sci. USA*. 74:5463.
20. Smeltzer, M. S., et al. 1993. Phenotypic characterization of xpr, a global regulator of extracellular virulence factors in *Staphylococcus aureus. Infect. Immun*. 61:919–925.
21. Smith, I. 1993. Regulatory proteins that control lategrowth development, p.785–800. In A. L. Sonenshein, J. A. Hoch, and R. Losick (ed.), *Bacillus subtilis* and other gram positive bacteria, ASM Press, Washington D.C.
22. Vandenesch, F., et al. 1991. A temporal signal, independent of agr, is required for hla but not spa transcription in *Staphylococcus aureus. J. Bacteriol*. 173:6313–6320.
23. Blake et al, 1984, A rapid sensitive method for detection of alkaline phosphatase-conjugated anti-antibody on Western blots, *Anal. Biochem*., 136:175–179.

24. Boylan et al, 1991, Genetic method to identify regulons controlled by non-essential elements: isolation of a gene dependent on alternate transcription factor $\sigma^B$ of *Bacillus subtilis, J. Bacteriol.*, 173:7856–7866.
25. Brendel et al, 1986, Terminators of transcription with RNA polymerase from *E. coli, J. Biomol. Struct. Dyn.*, 3:705–723.
26. Brendel et al, 1984, A computer algorithm for testing potential prokaryotic terminators, *Nucl. Acids Res.*, 12:4411–4427.
27. Chang et al, 1979, High frequency transformation of *Bacillus subtilis* protoplasts by plasmid DNA, *Mol. Gen. Genet.*, 168:111–115.
28. Cheung et al, 1994, A method to isolate RNA from gram-positive bacteria and Mycobacteria, *Anal. Biochem.*, 222:511–514.
29. Cheung et al, 1994, Diminished virulence of a sar⁻agr⁻ mutant of *Staphylococcus aureus* in the rabbit model of endocarditis, *J. Clin. Invest.*, 94:1815–1822.
30. Cheung et al, 1988, Variation in the expression of cell wall proteins of *Staphylococcus aureus* grown on solid and liquid media, *Infect. Immun.*, 56:1061–1065.
31. Cheung et al, 1994, Cloning and sequencing of sarA: a gene required for the expression of agr, *J. Bacteriol.*, 176:4168–4172.
32. Greene et al, 1995, Adhesion properties of mutants of *Staphylococcus aureus* defective in fibronectin-binding proteins and studies on the expression of fnb genes, *Mol. Microbiol.*, 17:1143–1152.
33. Haidenwang, 1995, The sigma factors of *Bacillus subtilis, Microbiol. Rev.*, 59:506–531.
34. Heinrichs et al, 1996, Characterization of the sar locus and its interaction with agr in *Staphylococcus aureus, J. Bacteriol.*, 178:418–423.
35. Heimann, 1995, Compilation and analysis of *Bacillus subtilis* sigmaA-dependent promoter sequences:evidence for extended contact between RNA polymerase and upstream promoter DNA, *Nucl. Acids Res.*, 23:2351–2360.
36. Jeon et al, 1995, Solution structure of the activator contact domain of the RNA polymerase a subunit, *Science*, 270:1495–1497.
37. Liu-Johnson et al, 1986, The DNA binding domains and bending angle of the *E. coli* CAP promoter, *Cell*, 47:995–1005.
38. Mager et al, 1995, Stress-induced transcriptional activation, *Microbiol. Rev.*, 59:506–531.
39. Miksch et al, 1995, Growth phase-dependent induction of stationary phase promoters of *Escherichia coli* in different gram-negative bacteria, *J. Bacteriol.*, 177:5374–5378.
40. Novick, 1990, The staphylococcus as a molecular genetic system, p. 1–40, In R. P. Novick (ed.), *Molecular Biology of the Staphylococci*, VCH, New York.
41. Novick et al, 1984, Control of pT181 replication. I. The pT181 copy control functions acts by inhibiting the synthesis of a replication protein, *EMBO. J.*, 3:2399–2405.
42. Perez-Martin et al, 1994, Promoters responsive to DNA bending: a common theme in prokaryotic gene expression, *Microbiol. Rev.*, 58:268–290.
43. Rao et al, 1995, In vitro transcription of pathogenesis-related genes by purified RNA polymerase from *Staphylococcus aureus, J. Bacteriol.*, 177:2609–2614.
44. Ross et al, 1993, A third recognition element in bacterial promoters:DNA binding by the $\alpha$ subunit of RNA polymerase, *Science*, 262:1407–1413.
45. Vicente et al, 1991, The role of the gearbox in the transcription of essential genes, *Mol. Microbiol.*, 5:2085–2091.
46. Waldvogel, 1985, *Staphylococcus aureus*, p. 1097–1116, In G. L. Mandell, R. G. Jr. Douglas, and J. E. Bennett (ed.), Principles and Practice of Infectious Diseases, John Wiley & Sons, New York.

All of the above references are incorporated by reference herein.

What is claimed is:

1. An isolated, purified full-length S. aureus staphylococcal accessory regulatory (sar) protein, wherein said protein regulates the expression of S. aureus exoprotein virulence determinants, and has an amino acid sequence of about 124 amino acids.

2. A sar protein according to claim 1, wherein the protein comprises the amino acid sequence of the wild-type sar protein of SEQ ID NO: 7.

3. A fragment of a sar protein according to claim 1, wherein said fragment is selected from the group consisting of the sarA protein, the ORF3 protein, and the sart protein.

4. A fragment of a sar protein according to claim 3, wherein said fragment consists of an amino acid sequence selected from the group consisting of SEQ ID NO: 12 and SEQ ID NO: 13.

5. An isolated, purified DNA molecule from S. aureus encoding a sar protein according to claim 1, wherein said DNA molecule consists of nucleotide sequences of the sar regulatory region.

6. A DNA molecule according to claim 5, wherein said DNA molecule encodes a sar protein which comprises the amino acid sequence of SEQ ID NO: 7.

7. A DNA molecule according to claim 5, wherein said DNA molecule encodes a sar protein which comprises an amino acid sequence which is degenerate to the sequence of SEQ ID NO: 7.

8. A DNA molecule according to claim 5, wherein said DNA molecule has a conservative mutation.

9. A replicable expression vector comprising a DNA molecule according to claim 5.

10. A replicable expression vector according to claim 9, wherein said DNA molecule is operably linked to elements required for its expression.

11. A replicable expression vector according to claim 10, wherein the nucleotide sequence element comprises a nucleotide sequence selected from the group consisting of a promoter, a transcription enhancer element, a termination signal, a translation signal, and a combination of two or more of these elements including a promoter.

12. A replicable expression vector according to claim 11, wherein the promoter is selected from the group consisting of trp, lac, $P_L$, and T7 polymerase.

13. A replicable expression vector according to claim 10, further comprising a selectable marker.

14. A replicable expression vector according to claim 10, wherein the vector is selected from the group consisting of plasmids, bacteriophages, cosmids, and viruses.

15. A replicable expression vector according to claim 10, wherein the expression vector comprises RNA.

16. An isolated, purified antibody to the sar protein of claim 1.

17. A composition comprising the antibody of claim 16 linked to a reporter molecule.

18. The composition of claim 17, wherein the reporter molecule is selected from the group consisting of enzymes, fluorophores, and radionuclide containing molecules.

19. A diagnostic method for detecting the presence of the sar gene in a microbial isolate, comprising extracting the DNA of the microbial isolate, and probing said DNA with a labeled gene probe constructed from a DNA molecule according to claim 5, wherein detection of hybridization is indicative of the presence of the sar gene in said microbial isolate.

20. An isolated, purified S. aureus staphylococcal accessory regulatory (sarA) protein, wherein said protein has a molecular weight from about 14.7 to about 14.8 kD, a pI of about 8.5, and an ammo acid sequence selected from the group consisting of SEQ ID NO: 7; SEQ ID NO: 12; and SEQ ID NO: 13.

21. A fusion protein comprising a sarA protein according to claim 20 linked to a heterologous protein.

22. An isolated, purified DNA molecule encoding a sarA protein according to claim 20.

23. A replicable expression vector comprising a DNA molecule according to claim 22.

24. A replicable expression vector according to claim 23, wherein said DNA molecule is operably linked to elements required for its expression.

25. A replicable expression vector according to claim 24, wherein said elements are selected from the group consisting of a promoter, a transcription enhancer element, a termination signal, a translation signal, and a combination of two or more of these elements including a promoter.

26. A replicable expression vector according to claim 25, wherein the promoter is selected from the group consisting of trp, lac, $P_L$, and T7 polymerase.

27. A replicable expression vector according to claim 26, further comprising a selectable marker.

28. The replicable expression vector of claim 23, wherein the vector is selected from the group consisting of plasmids, bacteriophages, cosmids, and viruses.

29. The replicable expression vector of claim 23, wherein the expression vector comprises RNA.

30. A diagnostic method for detecting the presence of the sar gene in a microbial isolate, comprising extracting the DNA of the microbial isolate, and probing said DNA with a labeled gene probe constructed from the DNA of claim 24, wherein detection of hybridization is indicative of the presence of the sar gene in said microbial isolate.

* * * * *

```
                           SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

TAAGTGACCA TTGATAACAA CTC                                              23

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)
```

(xi) SEQUENCE DESCRIPTION: SEQ ID NO:2:

TGTTTCGATA TTCAATGTGT GTC                                              23

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TGTCTATACG TTATTCCGAT TGA                                              23

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATCAGCGAAA ACAAAGAGAA AGAAT                                            25

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGTGCCATTA GTGCAAAAC                                                   19

(2) INFORMATION FOR SEQ ID NO:6:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 19..393

(xi) SEQUENCE DESCRIPTION: SEQ ID NO:6:

```
AATAGGGAGG TTTTAAAC ATG GCA ATT ACA AAA ATC AAT GAT TGC TTT GAG         51
                   Met Ala Ile Thr Lys Ile Asn Asp Cys Phe Glu
                    1               5                  10

TTG TTA TCA ATG GTC ACT TAT GCT GAC AAA TTA AAA AGT TTA ATT AAA         99
Leu Leu Ser Met Val Thr Tyr Ala Asp Lys Leu Lys Ser Leu Ile Lys
         15                  20                  25

AAG GAA TTT TCA ATT AGC TTT GAA GAA TTC GCT GTA TTG ACA TAC ATC        147
Lys Glu Phe Ser Ile Ser Phe Glu Glu Phe Ala Val Leu Thr Tyr Ile
     30                  35                  40

AGC GAA AAC AAA GAG AAA GAA TAC TAT CTT AAA GAT ATT ATT AAT CAT        195
Ser Glu Asn Lys Glu Lys Glu Tyr Tyr Leu Lys Asp Ile Ile Asn His
```

-continued

```
         45                  50                  55
TTA AAC TAC AAA CAA CCA CAA GTT GTT AAA GCA GTT AAA ATT TTA TCT        243
Leu Asn Tyr Lys Gln Pro Gln Val Val Lys Ala Val Lys Ile Leu Ser
 60                  65                  70                  75

CAA GAA GAT TAC TTC GAT AAA AAA CGT AAT GAG CAT GAT GAA AGA ACT        291
Gln Glu Asp Tyr Phe Asp Lys Lys Arg Asn Glu His Asp Glu Arg Thr
                     80                  85                  90

GTA TTA ATT CTT GTT AAT GCA CAA CAA CGT AAA AAA ATC GAA TCA TTA        339
Val Leu Ile Leu Val Asn Ala Gln Gln Arg Lys Lys Ile Glu Ser Leu
             95                 100                 105

TTG AGT CGA GTA AAT AAA CGA ATC ACT GAA GCA AAC AAC GAA ATT GAA        387
Leu Ser Arg Val Asn Lys Arg Ile Thr Glu Ala Asn Asn Glu Ile Glu
        110                 115                 120

CTA TAA                                                                393
Leu  *
    125
```

(2) INFORMATION FOR SEQ ID NO:7:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Thr Tyr Ala Asp Lys Leu Lys Ser Leu Ile Lys Lys Glu Phe Ser Ile
 1               5                  10                  15

Ser Phe Glu Glu Phe Ala Val Ile Ser Glu Asn Lys Glu Lys Glu Tyr
                20                  25                  30

Tyr Leu Lys Asp Ile Ile Asn His Leu Asn Tyr Lys Gln Pro Gln Val
            35                  40                  45

Val Lys Ala Val Lys
    50
```

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Tyr Leu Lys Lys Phe Ser Glu Glu Asn Glu Lys Leu Asp Ile Asn Leu
 1               5                  10                  15

Asn Val Lys
```

(2) INFORMATION FOR SEQ ID NO:9:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Ser Tyr Ser Glu Glu Lys Arg Gly Leu Asn Lys Lys Ile Phe Leu Leu
 1               5                  10                  15
```

```
Ser Glu Glu Glu Val Ser Ile Val Glu Lys Asn Ile Glu Lys Arg Trp
            20                  25                  30

Arg Leu Ser Asp Ile Ser Asn Asn Leu Asn Leu Ser Glu Ile Ala Val
        35                  40                  45

Arg Lys Arg Leu Glu
        50
```

(2) INFORMATION FOR SEQ ID NO:10:

(i) SEQUENCE CHARACTERISTICS:
    (A) LENGTH: 1349 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

```
AAAGCGTTGA TTTGGGTAGT ATGCTTTGAC ACAACAAATT TTAATTTAGC AAATTCGATA      60

GTCAACTCAT TCTTAAGACC TAAATTAATG TTATTTTTTA ATAATTTACA CCAAATTAAT     120

AGCAAAAATT ATGTTATTCG TGCTAATATT TCATAGTTGG TTATTCAATT AATTAAAAAT     180

AAGTCAAAAT GCACAACTTT TTATAATTCA TTGAGTCGAG TTTGAAAAAT AAAAGTGCTT     240

TAATGCATGA TCAATTATCG TACTTTCTAT TATTTGTTAC CCGTTATCAA TCGGAATAAC     300

GTATAGACAC TTTAACGTGC TATAGATTGG TTTTAATCAC TAAATTAATG TGTTTTTCTT     360

ATCATTAAAA CTGCACTGAG AATTACTAAA TTAAAAAAAT TATAAAAATT TTTCATTTTT     420

AGTGATAAAA TTCTGAAAAA TGGGTATAAA TAGTAGAAGA AGTTAACTTG GAAGAGTTAA     480

GCTATAACAA AGAATCTCTT TAGACACACA TTGAATATCG AAACATTTAA TTGCGCTAAA     540

TCGTTTCATT AAATAAATTA CCTTGTATTG TCGATTAAAT TAAGGTAAAT TATAAAAAAT     600

GCTGATATTT TTGACTAAAC CAAATGCTAA CCCAGAAATA CAATCACTGT GTCTAATGAA     660

TAATTTGTTT TATAAACACT TTTTTGTTTA CTTCTCATTT TTAATTAGTT ATAATTAACT     720

AAATAATAGA GCATTAAATA TATTTAATAA AACTTATTTA ATGCAAAATT ATGACTAACA     780

TATCTATAAT AAATAAAGAT TAGATATCAA TATATTATCG GGCAAATGTA TCGAGCAAGA     840

TGCATCAAAT AGGGAGGTTT TAAACATGAT GGCAATTACA AAAATCAATG ATTGCTTTGA     900

GTTGTTATCA ATGGTCACTT ATGCTGACAA ATTAAAAAGT TTAATTAAAA AGGAATTTTC     960

AATTAGCTTT GAAGAATTCG CTGTATTGAC ATACATCAGC GAAAACAAAG AGAAAGAATA    1020

CTATTTTAAA GATATTATTA ATCATTTAAA CTACAAACAA CCACAAGTTG TTAAAGCAGT    1080

TAAAATTTTA TCTCAAGAAG ATTACTTCGA TAAAAAACGT AATGAGCATG ATGAAAGAAC    1140

TGTATTAATT CTTGTTAATG CACAACAACG TAAAAAAATC GAATCATTAT TGAGTCGAGT    1200

AAATAAATGA ACTGAAGCAA ACAACGAAAT TGAACTATAA TTTTGTTTAG CGCAATTTGG    1260

TGAAGTTTGA TAGATGATAC ATTCTATTAA ACTTCCTTTT TTTATGCTCT TTTTACCTAA    1320

TTGTTAAGAG GTTTTGCACT AATGGCACT                                      1349
```

(2) INFORMATION FOR SEQ ID NO:11:

(i) SEQUENCE CHARACTERISTICS:
    (A) LENGTH: 342 base pairs
    (B) TYPE: nucleic acid
    (C) STRANDEDNESS: single
    (D) TOPOLOGY: linear (ii) MOLECULE TYPE: DNA (genomic)

(ix) FEATURE:
        (A) NAME/KEY: misc_feature
        (B) LOCATION: 157
        (D) OTHER INFORMATION: /note= "Nucleotide at position 157
            is N wherein N = C or T."

(ix) FEATURE:
        (A) NAME/KEY: misc_feature
        (B) LOCATION: 340
        (D) OTHER INFORMATION: /note= "Nucleotide at position 340
            is N wherein N = C or T."

(xi) SEQUENCE DESCRIPTION: SEQ ID NO:11:

ATGGCAATTA CAAAAATCAA TGATTGCTTT GAGTTGTTAT CAATGGTCAC TTATGCTGAC      60

AAATTAAAAA GTTTAATTAA AAAGGAATTT TCAATTAGCT TTGAAGAATT CGCTGTATTG     120

ACATACATCA GCGAAAACAA AGAGAAAGAA TACTATNTTA AAGATATTAT TAATCATTTA     180

AACTACAAAC AACCACAAGT TGTTAAAGCA GTTAAAATTT TATCTCAAGA AGATTACTTC     240

GATAAAAAAC GTAATGAGCA TGATGAAAGA ACTGTATTAA TTCTTGTTAA TGCACAACAA     300

CGTAAAAAAA TCGAATCATT ATTGAGTCGA GTAAATAAAN GA                        342

(2) INFORMATION FOR SEQ ID NO:12:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met Ala Ile Thr Lys Ile Asn Asp Cys Phe Glu Leu Leu Ser Met Val
1               5                   10                  15

Thr Tyr Ala Asp Lys Leu Lys Ser Leu Ile Lys Lys Glu Phe Ser Ile
            20                  25                  30

Ser Phe Glu Glu Phe Ala Val Leu Thr Tyr Ile Ser Glu Asn Lys Glu
        35                  40                  45

Lys Glu Tyr Tyr Leu Lys Asp Ile Ile Asn His Leu Asn Tyr Lys Gln
    50                  55                  60

Pro Gln Val Val Lys Ala Val Lys Ile Leu Ser Gln Glu Asp Tyr Phe
65                  70                  75                  80

Asp Lys Lys Arg Asn Glu His Asp Glu Arg Thr Val Leu Ile Leu Val
                85                  90                  95

Asn Ala Gln Gln Arg Lys Lys Ile Glu Ser Leu Leu Ser Arg Val Asn
            100                 105                 110

Lys Arg Ile Thr Glu Ala Asn Asn Glu Ile Glu Leu
        115                 120

(2) INFORMATION FOR SEQ ID NO:13:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Ala Ile Thr Lys Ile Asn Asp Cys Phe Glu Leu Leu Ser Met Val
1               5                   10                  15

Thr Tyr Ala Asp Lys Leu Lys Ser Leu Ile Lys Lys Glu Phe Ser Ile

```
            20                  25                  30
Ser Phe Glu Glu Phe Ala Val Leu Thr Tyr Ile Ser Glu Asn Lys Glu
            35                  40                  45

Lys Glu Tyr Tyr Phe Lys Asp Ile Ile Asn His Leu Asn Tyr Lys Gln
 50                  55                  60

Pro Gln Val Val Lys Ala Val Lys Ile Leu Ser Gln Glu Asp Tyr Phe
 65                  70                  75                  80

Asp Lys Lys Arg Asn Glu His Asp Glu Arg Thr Val Leu Ile Leu Val
                85                  90                  95

Asn Ala Gln Gln Arg Lys Lys Ile Glu Ser Leu Leu Ser Arg Val Asn
               100                 105                 110

Lys
```

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TTAATTGATT TATTAT                                                        16

(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

ATCATCTTCT TC                                                           12

(2) INFORMATION FOR SEQ ID NO:16:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAAGTATCAA C                                                           11

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CTCGTATTTT TTTCCTTCAA A                                            21

-continued (2) INFORMATION FOR SEQ ID NO:18:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..120

(xi) SEQUENCE DESCRIPTION: SEQ ID NO:18:

```
ATG CTG ATA TTT TTG ACT AAA CCA AAT GCT AAC CCA GAA ATA CAA TCA        48
Met Leu Ile Phe Leu Thr Lys Pro Asn Ala Asn Pro Glu Ile Gln Ser
            130                 135                 140

CTG TGT CTA ATG AAT AAT TTG TTT TAT AAA CAC TTT TTT GTT TAC TTC        96
Leu Cys Leu Met Asn Asn Leu Phe Tyr Lys His Phe Phe Val Tyr Phe
            145                 150                 155

TCA TTT TTA ATT AGT TAT AAT TAA                                       120
Ser Phe Leu Ile Ser Tyr Asn  *
            160                 165
```